United States Patent

Paradis

[11] Patent Number: 5,806,831
[45] Date of Patent: Sep. 15, 1998

[54] CONTROL OF FLUID FLOW WITH INTERNAL CANNULA

[76] Inventor: Joseph R. Paradis, P.O. Box 22238, Hilton Head Island, S.C. 29925

[21] Appl. No.: 345,481

[22] Filed: Nov. 28, 1994

Related U.S. Application Data

[63] Continuation-in-part of Ser. No. 135,673, Oct. 13, 1993, Pat. No. 5,509,433.

[51] Int. Cl.$^6$ .................................................. A61M 39/00
[52] U.S. Cl. ........................ 251/149.1; 604/167; 604/256
[58] Field of Search ............................. 251/149.8, 149.1, 251/149.6; 604/905, 256, 167

[56] References Cited

U.S. PATENT DOCUMENTS

| | | |
|---|---|---|
| 4,429,856 | 2/1984 | Jackson . |
| 4,512,766 | 4/1985 | Vailancourt . |
| 4,915,687 | 4/1990 | Sivert . |
| 5,006,114 | 4/1991 | Rogers et al. . |
| 5,064,416 | 11/1991 | Newgard et al. . |
| 5,085,645 | 2/1992 | Purdy et al. .................. 604/256 X |
| 5,147,333 | 9/1992 | Raines . |
| 5,203,775 | 4/1993 | Frank et al. .................. 251/149.1 X |
| 5,242,393 | 9/1993 | Brimhall et al. . |
| 5,269,711 | 12/1993 | Thomas et al. . |
| 5,273,533 | 12/1993 | Bonaldo . |
| 5,300,034 | 4/1994 | Behnke et al. .................. 604/256 X |
| 5,306,243 | 4/1994 | Bonaldo . |
| 5,380,306 | 1/1995 | Brinon . |
| 5,474,536 | 12/1995 | Bonaldo . |
| 5,487,728 | 1/1996 | Vaillancourt . |
| 5,514,116 | 5/1996 | Vaillancourt et al. . |
| 5,549,566 | 8/1996 | Elias et al. . |
| 5,549,577 | 8/1996 | Siegel et al. . |
| 5,616,130 | 4/1997 | Mayer .................................. 604/167 X |

FOREIGN PATENT DOCUMENTS

| | | |
|---|---|---|
| 0309771 | 9/1988 | European Pat. Off. . |
| 9311828 | 6/1993 | WIPO . |

Primary Examiner—Kevin Lee
Attorney, Agent, or Firm—Brooks Haidt Haffner & Delahunty

[57] ABSTRACT

A flexible container for medical fluid including a flexible housing with an adapter secured to the housing for connecting an outlet to a complementary inlet of another container sealed by a stopper having an outlet connected to an inlet and disposed to serve as a conduit for fluid flow, with a movable member sealing the inlet and having a flexible body for controlling flow by the extent to which the flexible body is buckled and the removal of flex restores the seal; the stopper can take the form of a flow control device with an inlet for fluid and a slotted movable member sealing the inlet and closing the slot, with the unsealing of the inlet and the opening of the slot permitting the passage of fluid to an outlet, advantageously through a cannula that is surrounded by the opened slot and extends to the outlet; a member external to the flow control device, such as the tip of a Luer taper, can activate the moveable member by depressing it to allow the flow of fluid.

22 Claims, 18 Drawing Sheets

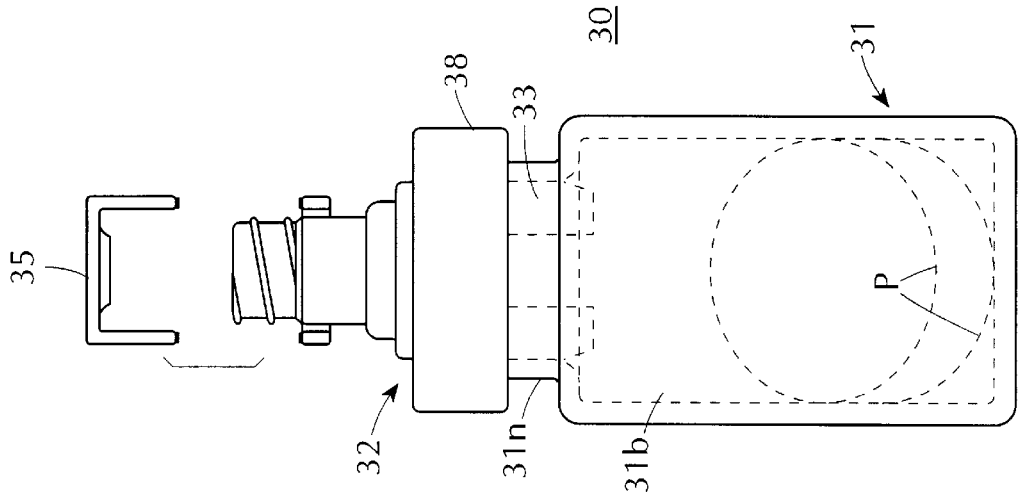
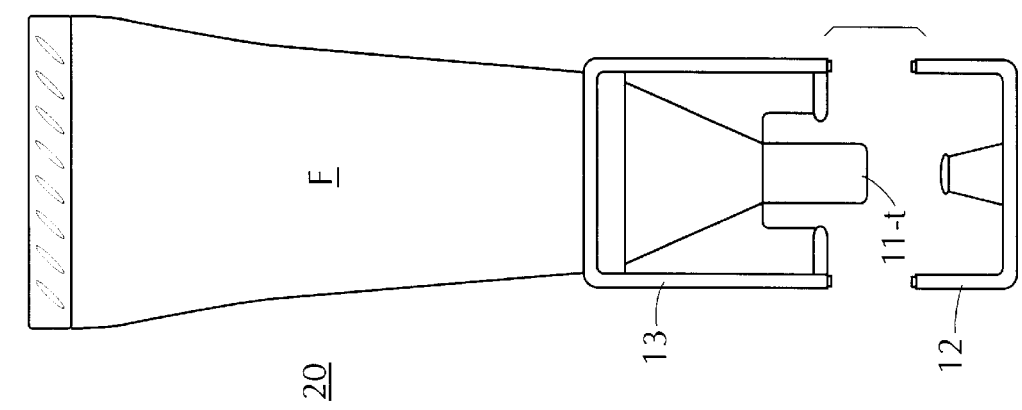

CONTROL OF FLUID FLOW WITH INTERNAL CANNULA

This is a continuation-in-part of Ser. No. 08/135,673 filed Oct. 13, 1993, U.S. Pat. No. 5,509,433.

BACKGROUND OF THE INVENTION

The invention relates to the transfer of fluids and more particularly, to the transfer of fluids between containers of medical solutions, and with respect to the infusion and aspiration of fluids in venous and arterial systems.

A common container for medical fluids is a plastic pouch which contains saline, i.e. a salt solution used in investigation of biological and physiological processes. Such a container is "spiked", i.e. pierced by a projection, in order to access its contents which are carried by a conduit, typically plastic tubing through a "check" valve that is used to prevent back flow to the spiked container. In addition, other check valves can be used with the conduit to provide for the infusion and/or aspiration of other substances, such as medicaments, body fluids, and anesthetics. Infusion is commonly used to introduce saline or other medical fluids into veins, while aspiration is commonly used to draw fluids from body cavities.

The ordinary check valve used with conduits from medicinal containers functions by the deflection of an elastomeric element towards and away from a valve seat. The deflection is towards the valve seat in order to prevent flow, and away from the seat to permit flow.

Because the conventional saline bag is spiked, removal of the spiking connector may be difficult. Unless the bag is inverted, there will be leakage when the spike is withdrawn.

Another common container for medical fluids is the glass vial which is commonly accessed by needle. It would be desirable to access such vials without the need for using needles, which can cause inadvertent injuries to medical personnel. In addition, glass vials and commonly used medical storage containers are relatively inflexible, and it would be desirable to be able to employ flexible medical storage containers without the need for spiking the container, as is customary for the storage, for example, of saline.

Because of the desirability of avoiding spiking and achieving needleless injection and infusion of fluids, one effort has resulted in Rogers et al. U.S. Pat. No. 5,006,114 of Apr. 9, 1991 in which a valve assembly has a Luer lock on an inlet, and a movable piston seals the inlet.

When a syringe is attached to the Rogers inlet the piston is displaced to unseal a fluid channel which connects the end of the syringe to an outlet, and then to a device connected to a patient. When the syringe is removed from the inlet the piston is moved to its original closed position by an internal spring of the valve. This device suffers from the disadvantage that the requirement of a spring for acting against the piston results in a force against the inserted Luer tip that increases as the piston is displaced.

In addition, the Rogers medical valve assembly provides an outlet channel that is displaced at an angle in relation to the inlet. As a consequence of this angular displacement, it is difficult to manufacture the device since there is a tendency for flash to accumulate at the entrance of the outlet channel in the vicinity of the piston. In addition, the angular configuration of the Rogers valve does not lend itself to manifold application.

Moreover, the Rogers design is intended for a Luer fitting which does not have a taper so that when the conventional tapered Luer fitting is employed, it can become jammed in the straight line walls of the inlet.

An attempt to overcome the disadvantages of Rogers is disclosed in Raines, U.S. Pat. No. 5,147,333, which issued Sep. 15, 1992. In the Raines patent there is accommodation for a tapered Luer fitting, but there is the continued disadvantage of the necessity for using a spring to urge a piston or spool forwardly during closure of the valve and rearwardly when the valve is being opened.

As a result, the disadvantageous increase in spring force with displacement continues to be present. Furthermore, the Raines "backcheck" valve requires a pair of vertically offset ports that extend laterally from a tubular body and the spool or piston is disposed between the ports. In addition, like the predecessor Rogers valve, the piston or spool in Raines requires at least one projection from the end of the piston contacted by a Luer tip in order to permit the flow of fluid from the Luer tip through the valve.

Furthermore, like the Rogers predecessor, the Raines valve is subject to difficulties in manufacture because of flash since the various outlet ports are angularly, i.e., perpendicularly, oriented in relation to their inlets.

Other arrangements are disclosed in Newgard, U.S. Pat. No. 5,064,416; Sivert, U.S. Pat. No. 4,915,687 and Jackson, U.S. Pat. No. 4,429,856. Those arrangements are complex and difficult to manufacture with numerous disadvantages.

Another objection to existing arrangements is that their activators are not interchangeable. In addition, current non-needle injection sites present problems of sterility. For such sites, it is necessary to have an open channel that can become contaminated. Even when a temporary seal is provided for the open channel, removal of the seal prior to use allows inadvertent contamination. This is by contrast with a site having a surface that can be wiped clean with a sterilizing agent before usage is to take place.

Accordingly, it is an object of the invention to achieve needleless transfer of fluids without the need for spring-loaded members, such as pistons or spools where the counterforce exerted by the spring increases as the piston is displaced. A related object of the invention is to overcome the disadvantages characterizing the needleless injection valves of Rogers, U.S. Pat. 5,006,114 and Raines, U.S. Pat. No. 5,147,333.

A further object of the invention is to achieve needleless transfer of fluids from flexible container, as well as obtain access to glass vials without the need for using needles.

Yet another object of the invention is to avoid the use of projections on a closure for an inlet, whereby a Luer fitting can open an inlet channel without the need for engaging one or more projections on a closure.

A further object of the invention to enhance the control that can be achieved over fluid flow. A related object is to enhance flow control where fluid is to be transferred from one container to another.

An important object of the invention is to eliminate the need for needle usage with medical containers. A related object is to maintain sterility at sites that are operated without needles.

An additional object of the invention is to improve the performance of valves for fluid transfer and control of fluid flow.

A further object of the invention is to achieve tamper evident arrangements for components used in the infusion and aspiration of medicinal fluids.

SUMMARY OF THE INVENTION

In accomplishing the foregoing and related objects the invention provides a flexible container for medical fluid including a flexible housing with an outlet and an integrated adapter for connecting the outlet to a complementary inlet of another container.

In accordance with one aspect of the invention, the adapter is a rectangular frame integrated with the outlet, and the adapter has a partial Luer thread, which straddles the outlet. The rectangular frame integrated with the outlet can contain a partial Luer thread and be sealed by a frangible connector integrated with the rectangular frame. The outlet of the flexible container is configured with Luer taper.

In accordance with another aspect of the invention, a stopper for sealing a container of medical fluid has an inlet for the flow of fluid, an outlet connected to the inlet and disposed with respect thereto to serve as a conduit for fluid flow, and a movable member sealing the inlet and having a flexible body for controlling flow by the extent to which the flexible body is buckled. As a result, access to the container, with the stopper thereon, is achieved by flexing the movable sealing member to unseal the container, and the removal of flex restores the seal of the container. The movable member can extend between the inlet and outlet and is expandable laterally with respect to the axis of the outlet in order to control said flow.

In accordance with a further aspect of the invention, the stopper further permits activation of the movable controlling member by a member external thereto, wherein the moveable member terminates in a plug seated in the inlet and can be depressed from its seat. The movable controlling member can be bell-shaped with its upper portion sealing the inlet and having walls straddling the outlet. The extending member is bowed under pressure in the axial direction of the outlet.

In a method of permitting the transfer of fluids according to the invention, the steps include (1) sealing a container by a flexible stopper; and (2) controllably flexing the stopper to permit the flow of fluid with respect to the container. The flexible stopper can have Luer connector threads and the method further include the step of engaging the Luer threads by complementary Luer threading.

In accordance with one aspect of the method, a frangible cover is removed from the stopper before the flexing thereof. Another frangible cover is removed from the complementary Luer threading before engagement with the Luer threads.

The method further includes the step of flexing the stopper by applying fluid pressure thereto, and the stopper is positioned on a container for medicinal fluid in order to permit access to the container by flexing the stopper, and resealing of the container is accomplished by unflexing the stopper.

In further accomplishment of the foregoing and related objects the invention also provides a flow control device with an inlet for the flow of fluid, an outlet connected to the inlet and disposed for flow into the inlet and a movable member having an apertured and compressible head for sealing the inlet and engageable with a closed conduit extending to the outlet. The movable member also has a flexible body and an inlet slit which is opened by the closed conduit that extends to the outlet for permitting flow through the head to the outlet when the inlet is unsealed.

In accordance with one aspect of the invention, the inlet extends to a tapered bore which is spaced from the movable member, and the aperture of the head is opened when the head is moved to the tapered bore to engage the conduit. The tapered bore can extend to a further bore within which the flexible body is collapsible and laterally expansible with respect to the axis of the outlet. The flexible body can be rectangular in cross-section.

In accordance with another aspect of the invention, activation of the movable member can be accomplished externally to the flow control device, for example, by the tip of a Luer taper which seals on the top surface of the head as it unseals the inlet by depressing the head of the movable member into contact with an internal blunt cannula to open an aperture in the head.

The head may include outwardly tapered walls so that the taper of the head promotes the sealing of the inlet, and the slot of the head advantageously is in the form of a knife slit.

In a method of controlling fluid flow in accordance with the invention, the steps include (1) sealing an inlet by an apertured flexible stopper which contracts as it moves into the tapered inlet and closes the aperture of the stopper; and (2) depressing the stopper to contact an internal cannula and allow the aperture to open and permit the flow of fluid through the cannula. The stopper can be depressed by applying the tip of a Luer taper which can seal a circumferential area on top of the stopper. The depression of the stopper allows its expansion by the internal cannula to open the slot to permit the throughpassage of fluid.

The method of the invention further includes wiping the side wall of the region into which the stopper is expanded during its depression, and following the return of the stopper to its equilibrium position. The method can further include the step of causing fluid to flow through a closed channel to an outlet.

In a method of fabricating a flow control device, the steps include (a) molding a rectangular inlet member having an axis of flow, an inlet, a coaxial seat beyond the inlet, and an expansion chamber beyond the coaxial seat; (b) molding a rectangular outlet member which complements the inlet member and has a rectangular coaxial support and an internal cannula surrounding the outlet and extending inwardly therefrom; (c) inserting an apertured, expandable and rectangular control member into the inlet member; and (e) joining the outlet member to the inlet member with the expandable control member against the outlet support and surrounding the internal cannula.

The control member can be molded of an elastomeric material with opposed legs.

In further accomplishment of the foregoing and related objects, the invention provides a deformable elastomeric disk that is fixedly or non-fixedly disposed between inlet and outlet members. The fixed disk is deformable by pressure or by at least one integrated arm that extends from the inlet to the disk to permit flow through the inlet to the outlet, and a member is spaced from the disk for limiting the deformation in the direction of pressure through the outlet to the disk. The non-fixed disk is movable by pressure, or by at least one integrated arm that extends from the inlet to the disk, away from its seat.

In accordance with one aspect of the invention, the elastomeric disk is circular, positioned upon the outlet member between the inlet and outlet members and clamped or biased.

In accordance with another aspect of the invention the disk can have a slit therein, which can be linear or nonlinear, to permit the desired deformation.

A method of controlling fluid flow in accordance with the invention, may include deforming an elastomeric disk fixedly or non-fixedly disposed between inlet and outlet members by moving at least one arm extending from the inlet to the vicinity of the disk into contact with the disk to permit flow through the inlet member.

DESCRIPTION OF THE DRAWINGS

FIG. 3A is an elevation view of the flexible medicinal container of FIG. 2, after its tamper-evident seal cap has been removed, in accordance with the invention;

FIG. 3B is an elevation view of a stoppered medicinal vial in accordance with the invention, after its tamper-evident seal has been removed;

DETAILED DESCRIPTION

First Embodiments

Figure 1A:
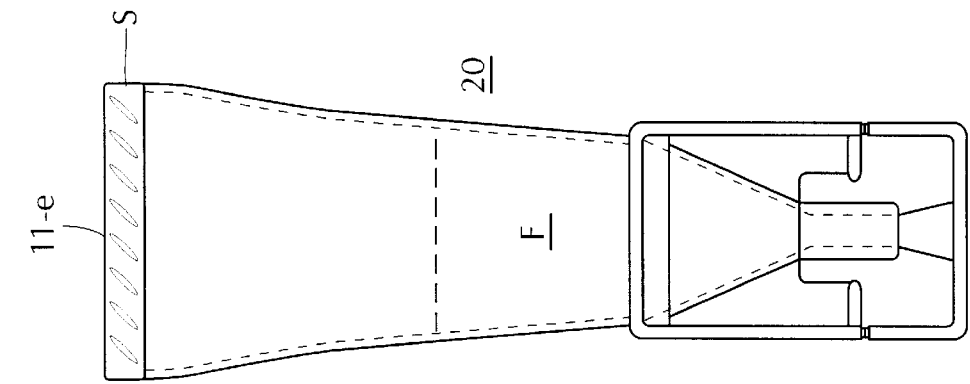
FIG. 1A is an elevation view of a flexible medicinal container, as molded, with an outlet in accordance with the invention.

With reference to the drawings, a flexible medicinal container 10 is formed by a cylindrical tube 11 that is sealed to a tamper-evident cap 12, as shown in FIG. 1A. The region of the container 10 where the cap 12 is sealed to the tube 11 includes a rectangular frame 13 with a partial Luer thread 14 that straddles the tapered Luer outlet 11-*t* which extends from the conical connector 11-*c* attached to the body 11-*b* of the tube 11.

The tamper-evident cap 12 has legs 12-1 and 12-2 that attach to corresponding legs 13-1 and 13-2 of the frame 13 at frangible joints 12*a*1 and 12*a*2. A further frangible joint 12*j* extends from the cross-bar 12*c* of the cap 12 into contact with the outlet access 11-*o* of the Luer taper 11-*t*.

The flexible container 10 has been given the trademark designation LUERPOD™.

Figure 1B:
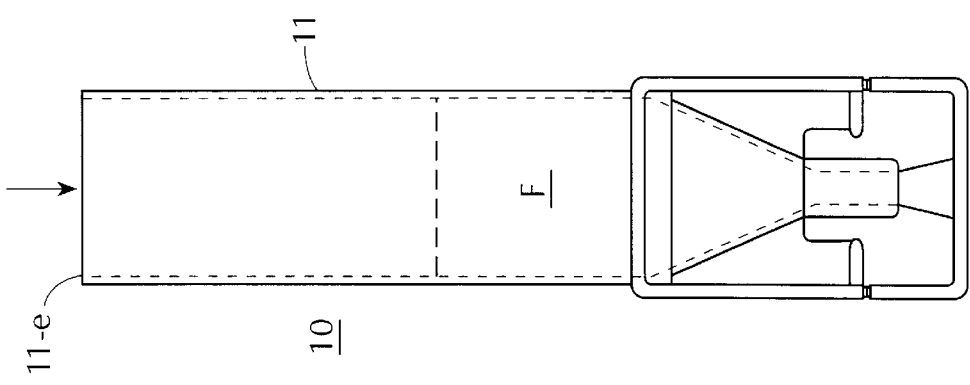
FIG. 1B is an elevation view of a flexible medicinal container, filled with fluid, with an outlet in accordance with the invention.
Figure 2:
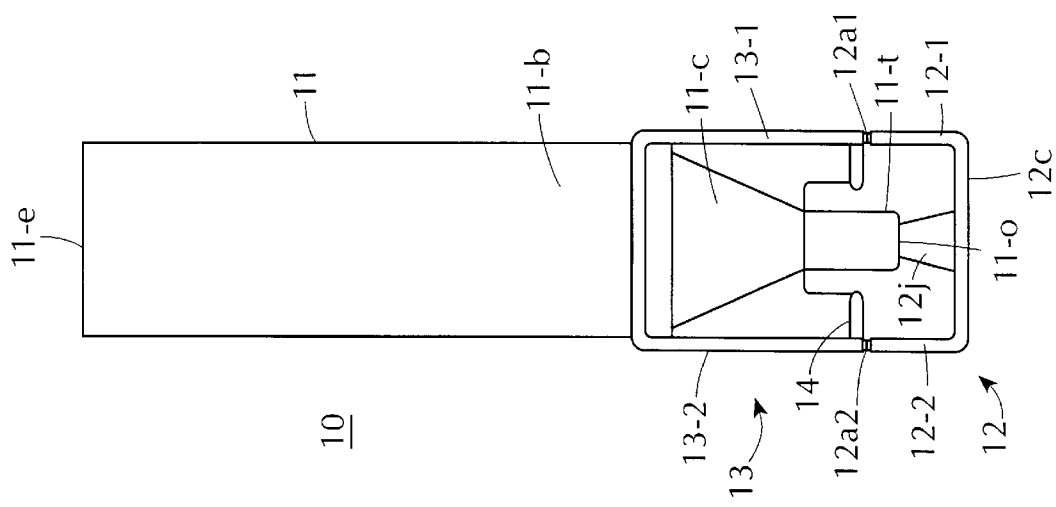
FIG. 2 is an elevation view of the flexible medicinal container of FIG. 1B, after being sealed, in accordance with the invention.

After the LUERPOD™ container 10 is molded, it is filled with fluid F, as shown in FIG. 1B. Since the tube 11 is a molded cylinder with an open end 11-*e*, filling takes place at that end as indicated. Following filling, the end 11-*e* is hermetically sealed by closing the end 11-*e*, and applying heat to form the seal S shown in FIG. 2.

The result is a hermetically sealed and flexible container 20 that can be used for the convenient storage of medical fluids, and can be accessed simply and conveniently as demonstrated below.

In particular, as shown in FIG. 3A, the tamper-evident cap 12 of the container 20 is twisted from the frame 13, in preparation for inserting the Luer taper 11-*t* into an appropriate container for the transfer of the fluid F into the other container.

An appropriate other container 30 is provided as shown in FIG. 3B by the glass vial 31, which is standard, and has a circular cross-section (not shown), with a body 31*b* extending to an inlet rim 31*r* by a neck 31*n*. Sealed to the rim 31*r* (shown in FIG. 5B and FIG. 6), by a neck 31*n*. Sealed to the rim 31r is a housing 32 that contains a stopper 33 which includes a valve member 34 (not visible in FIG. 3B) of the invention. The housing 32 normally carries a tamper-evident seal 35, which has been shown broken away in FIG. 3B in anticipation of the connection of the tube 20 to the container 30.

Figure 4C:
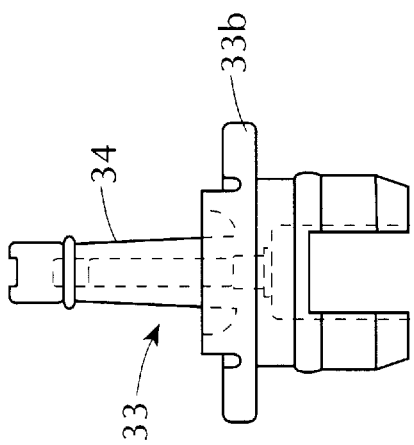
FIG. 4C is elevation view of the plug seal stopper for the for stoppered medical vial of FIG. 3B.
Figure 4B:
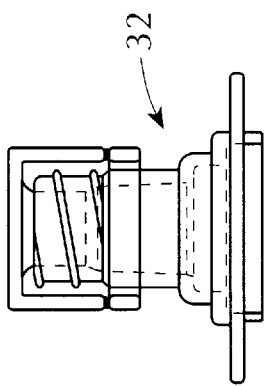
FIG. 4B is elevation view of the housing for the for stoppered medical vial of FIG. 3B.
Figure 4A:
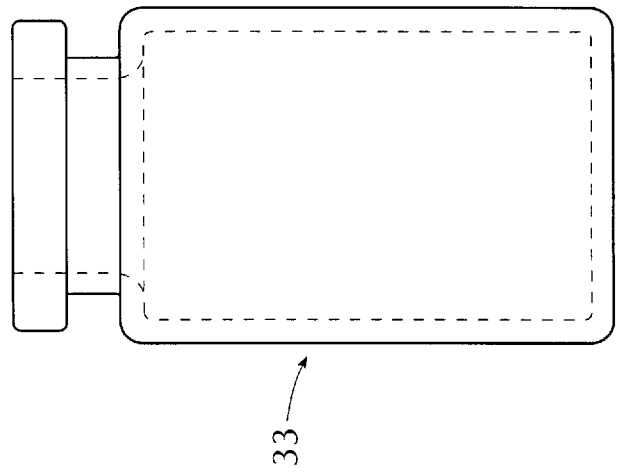
FIG. 4A is elevation view of the standard glass vial for the for stoppered medical vial of FIG. 3B.
Figure 6:
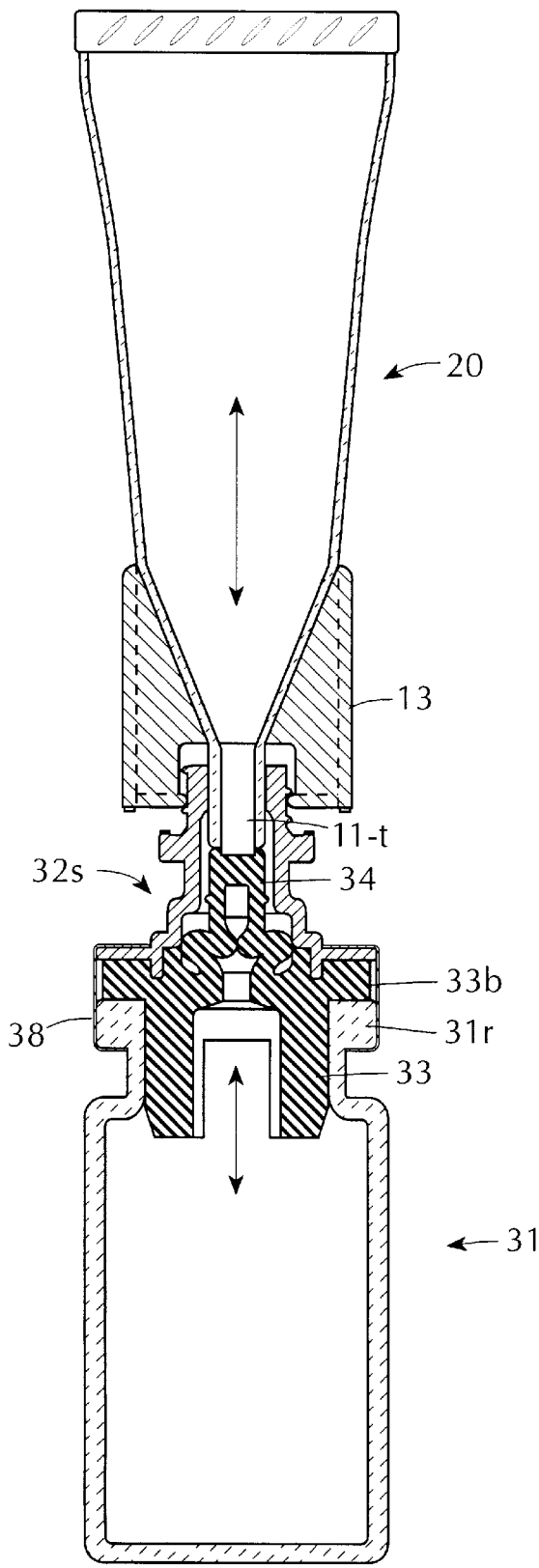
FIG. 6 is a section view of the flexible medicinal container of FIG. 3A, after removal of its tamper-evident seal cap, connected to the stoppered medical vial of FIG. 3B, for the transfer of fluid in accordance with the invention.

The glass vial 31, shown in FIG. 4A, is sealed by the housing 32, shown in FIG. 4B, that contains the stopper 33, shown in FIG. 4C, extending from a base 33b and includes a valve 34 of the invention, as shown operationally in the cross-sectional view of FIG. 6. The inlet stem 32s and the base 33b of the stopper 33 are held to the rim 31r by a locking collar 38, as shown in FIG. 3B and FIG. 6, and known in the art.

Figure 5A:
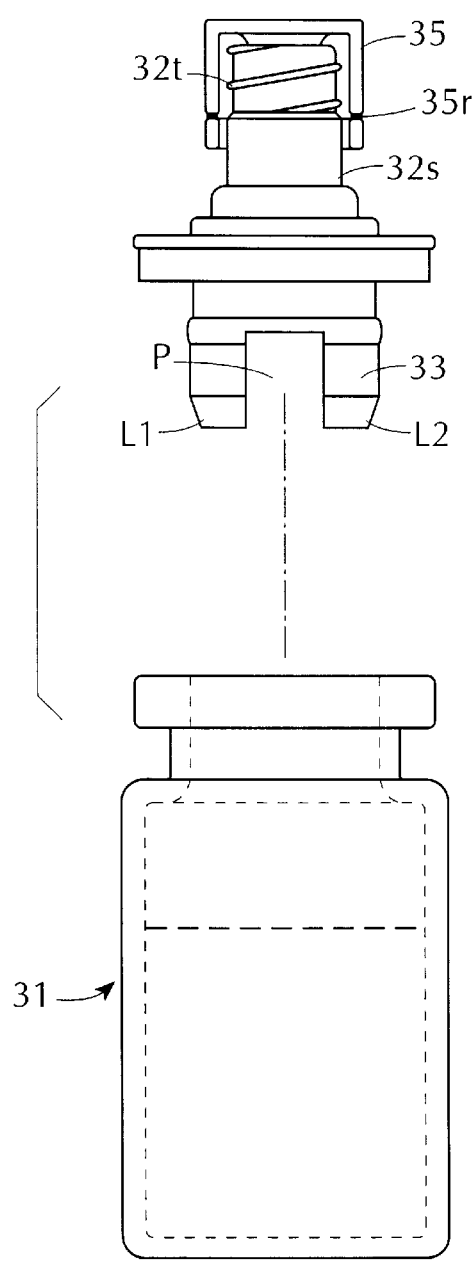
FIG. 5A is elevation view showing the combined housing and seal plug stopper of FIGS. 4A and 4B being inserted into the vial of FIG. 4C.

The stopper 33, shown being placed in the vial 31 in FIG. 5A, has opposed legs L1 and L2 straddling a spaced interval P. The housing 32 also has an inlet stem 32s which illustratively includes an exterior set of Luer threads 32t. The access opening of the inlet stem 32s is initially blocked by a tamper-evident seal and cap 35.

The seal and cap 35 illustrated in FIG. 3B is similar to the tamper-evident cap 12 of FIGS. 1A, 1B, 2 and 3A. When access is desired to the interior of the vial 31 by way of the stopper 33, the cap 35 is broken away at frangible regions 35r with the result that a Luer fitting can be threaded upon the inlet stem 32s, as illustrated in FIG. 6.

Figure 5B:
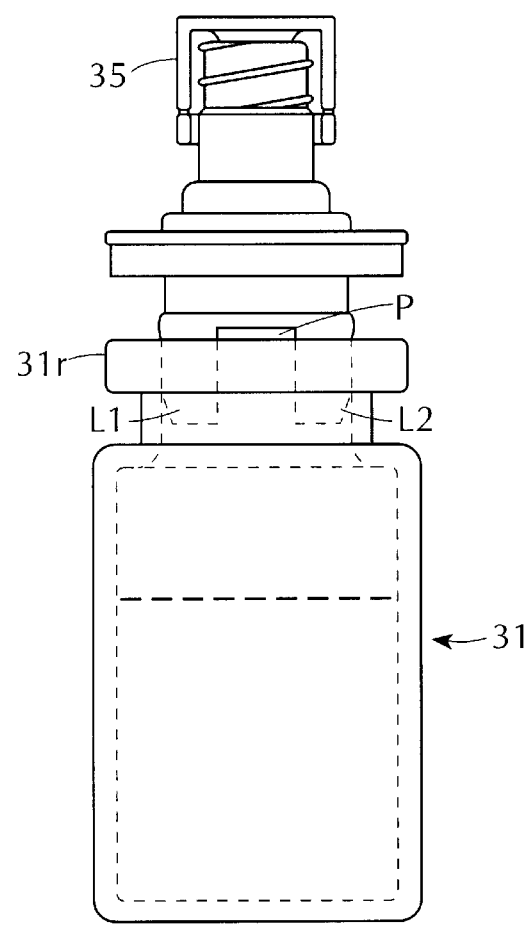
FIG. 5B is an elevation view of the combined housing and seal plug stopper partially inserted into the vial for vacuum processing.

As shown in FIG. 5B, the stopper 33, with the tamper-evident cap 35, is inserted into the container 31 at the rim 31r. The stopper 33 is initially only partially inserted into the container 31, so that the slot P between the legs L1 and L2 allows access to the interior of the container 31. This permits the container 31 to be evacuated before the stopper 33 is sealed to the container 31.

For example, the container 31 may have ingredients that require freeze drying by pulling a vacuum. Once there is sufficient vacuum, the stopper 33 is depressed into the rim 31r until the base 33b is in contact as shown in FIG. 6.

As noted above, the stopper 33 contains a flow control valve 34, which is illustrated in the cross-sectional view of FIG. 6. The valve structure 34 of the stopper 33 extends from the base 33b along the interior of the inlet stem 32s. As indicated in FIG. 3B, when access to the container 31 is desired, the sub-cap of the tamper evident seal 35 is twisted away. This permits access to the interior valve 34 by the Luer taper 11-t of FIGS. 1A, 1B, 2, 3A and 6. The action of the Luer fitting 11-t in operating the valve 34 is illustrated in FIG. 6.

In addition to the medicinal bottle 31 of FIGS. 3B and 6, the invention can be applied to a standard infusion bag (not shown). In place of the conventional spikable inlet, a housing, similar to the housing and stopper combination 32–33 of FIGS. 3B and 5A is attached to the bag. Access to the bag is by way of a standard Luer fitting which operates as illustrated for the embodiment of FIG. 6. The Luer fitting is connected to a conduit, illustratively plastic tubing, which extends to a check valve which can be of the kind illustrated in FIG. 6, and is suitable for needleless infusion as well.

In the case of the ordinary spiked bag, when the connector is removed after spiking has taken place, there is inevitable leakage because there is nothing to prevent flow from the interior of the bag. In the case of the invention, however, the removal of the Luer fitting does not produce any leakage because the valve 34 of the stopper 33 closes the outlet from the bag.

The valve 34 of the stopper 33 can be a movable and flexible plug which seals the inlet and extends to a flexible body for controlling flow by the extent to which the flexible body of the movable plug is buckled as indicated in FIG. 6. In effect, the combination of the plug and the body form a bell-shaped member with a slotted and fluted side walls. The base of the body terminates in a circumferential base ring.

The movable plug and the flexible body extend between an inlet and outlet. The flexible body of the movable plug is expandable laterally with respect to the flow axis of the outlet channel in order to control flow. Consequently the stopper has an enlarged expansion chamber. In addition, the stopper has a neck with exterior Luer threads and an interior undercut rim. A ring of the plug initially seals against the undercut rim and remains in contact with the interior wall of the neck as the plug is depressed until until the expansion chamber is reached. The upper portion of the expansion chamber has an undercut which permits outlet flow.

For the embodiment of FIG. 6, the plug 34 has an upper slot so that when a Luer tip, such as the tip 11-t, is threaded on the neck, there is no impediment to flow from the interior of the tip. This embodiment is particularly useful for relative low pressure infusion of fluids, e.g. by flow from the container 10 of FIG. 6. It is to be noted that because of the slot, pressure against the outer surface of the plug does not cause a collapse of the plug material which could block the tip 11-t.

The Luer tip 11-t thus permits activation of the control plug by a member external to the stopper 33 since the plug is seated in an inlet and can be depressed from its seat against an undercut rim.

In effect the control is by a bell-shaped member with its upper portion sealing the inlet, and walls straddling the outlet. The walls are extended legs which are bowed under pressure in the axial direction of the outlet channel. The slotted walls extend from a head sealing the inlet to a base encircling the outlet channel. The head can have a level surface at the entrance to the inlet for high pressure anesthetic applications, or an interrupted surface at the entrance to the inlet.

The stopper 33 can seal a container of medicinal fluid, and access to the container is achieved by flexing the movable seal to unseal the container, and the removal of flex restores the seal of the container.

In a method of the invention for controlling fluid flow the steps include (1) sealing an inlet of a flexible stopper; and (2) controllably flexing a slotted body extending integrally from the end of stopper to permit the flow of fluid to an outlet.

The method further includes the step of flexing the body of the stopper by applying fluid pressure. Alternatively, the body can be flexed by applying mechanical pressure.

The method of the invention also including the step of positioning the stopper at the inlet of a container for medicinal fluid in order to permit access to the container by flexing the stopper and resealing the container by unflexing the stopper. The step of flexing the stopper includes the lateral expansion of the body with respect to the flow axis of the inlet and outlet.

In a method of fabricating a flow control device by the invention the steps include (a) molding an inlet member having an axis of flow A, a coaxial seat and an expansion chamber; (b) molding an outlet member having the same axis of flow and a coaxial support; (c) inserting an expandable control member into the inlet with respect to the seat; and (e) joining the outlet member to the inlet member with the support for the expandable control member against the outlet member. The method further includes the step of molding the control member of an elastomeric material and, where the control member extends longitudinally, there is the further step of longitudinally slotting the control member. The control member can have a circular body with slots that are uniformly spaced about the body.

The component elements of the various devices can be joined, for example, by ultrasonic welding. The invention promotes sterility by providing ease of accessibility. Prior art valves with recessed stoppers allow antimicrobial agents to accumulate in puddles on the tops of stoppers. Particulate matter may also collect on recessed tops.

An alternative flow control device in accordance with the present invention has the same general structure described above, except that the plug has a level top surface. This device is intended for medical applications which involve the entry of fluids, for example in anesthesia, under relatively high pressures. As a result, after the Luer fitting is attached, the force of the applied fluid causes the plug to move downwardly and permit the flow of fluid into the outlet between ribs in the same fashion as illustrated.

The stopper 32 has been given the trademark designation INFUSAFE™ and allows the transfer of fluids without the use of needles. An INFUSAFE™ container can initially be empty and filled, either partially or completely, or may initially be filled and emptied, either partially or completely.

Second Embodiments

Figure 7A:
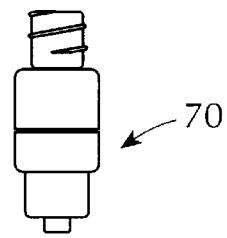
FIG. 7A is a scale view of one side of a flow-control valve in accordance with the invention for use with Luer fittings, such as that of FIGS. 1A and 1B.
Figure 7B:
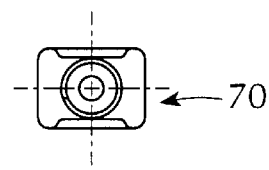
FIG. 7B is a scale view of the top side of the flow-control valve of FIG. 7A for use with Luer fittings.

With reference to FIG. 7A, there is shown a scale view of one side of a flow-control valve 70 in accordance with the invention for use with a Luer fitting, such as that of FIGS. 1A and 1B. A scale view of the top side of the flow-control valve 70 of FIG. 7A for use with Luer fittings is shown in FIG. 7B, and FIG. 7C is a scale view of the adjoining side of the flow-control valve 70 of FIG. 7A for use with Luer fittings.

Figure 7C:
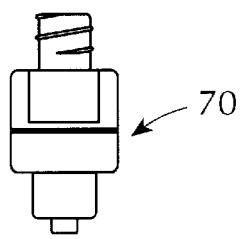
FIG. 7C is a scale view of the adjoining side of the flow-control valve of FIG. 7A for use with Luer fittings.

The valve 70 is rectangular in cross-section having the specific configuration described in detail below, with FIG. 7A showing the narrower side and FIG. 7C showing the wider side.

Figure 8A:
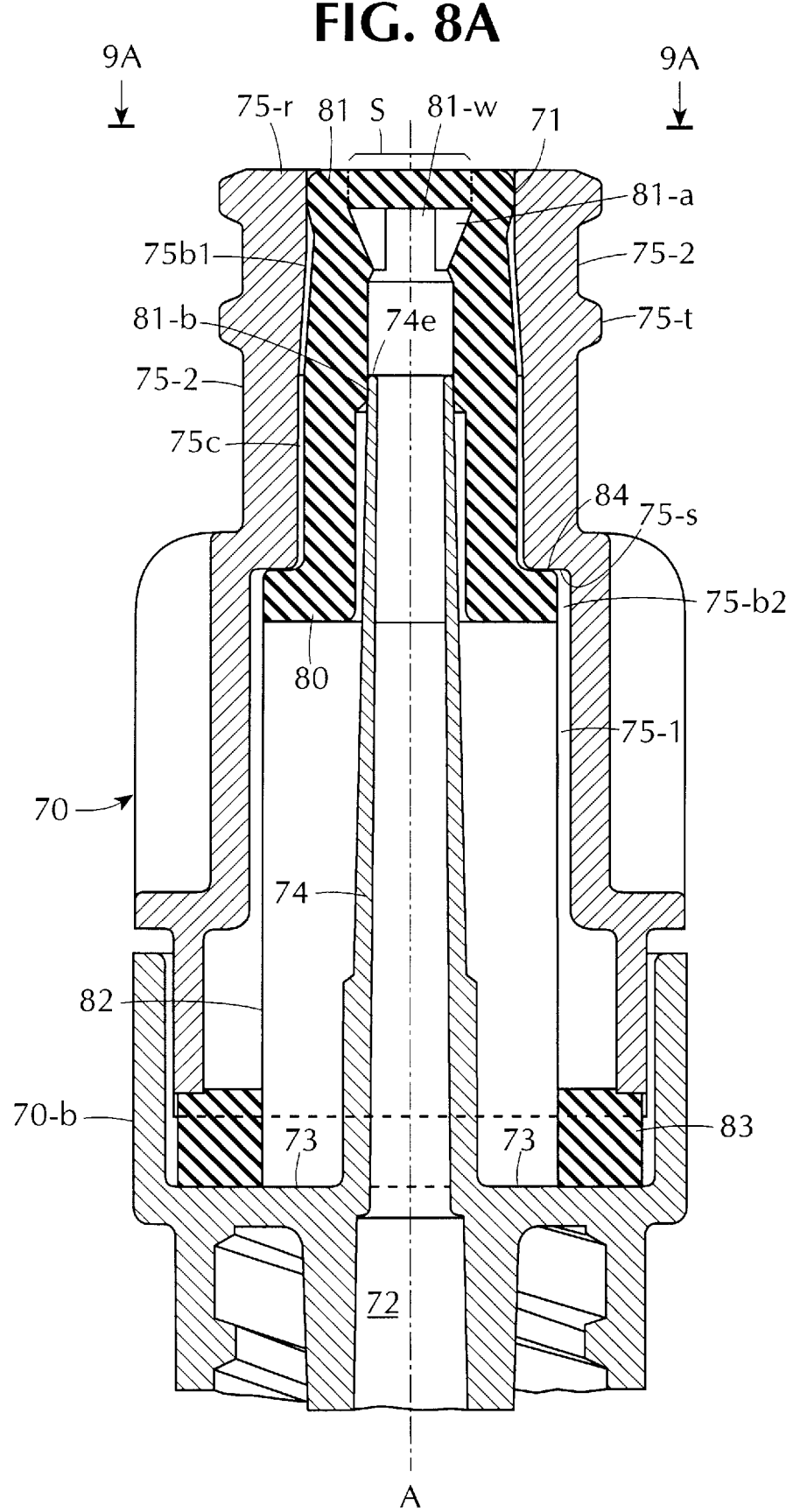
FIG. 8A is a partial, enlarged sectional view of the flow-control valve of FIG. 7C in its closed valve position.

In FIG. 8A, which is an enlarged sectional view, the flow-control valve 70 is shown in its "pre-loaded" condition with its inlet 71 sealed by the head 81 of a depressible plug 80. As indicated in FIG. 8A, the head 81 of the plug 80 has a closed slit S. In addition, the valve 70 has an outlet 72 extending to the inlet 71 and disposed to serve as a conduit for the throughflow of fluid that is applied at the inlet 71. In the embodiment of FIG. 8A, the head 81 of the plug 80 is flush with the circumferential end wall of the inlet 71. This facilitates antiseptic swabbing of the head before the plug is depressed by, for example, a Luer tip.

Figure 8B:
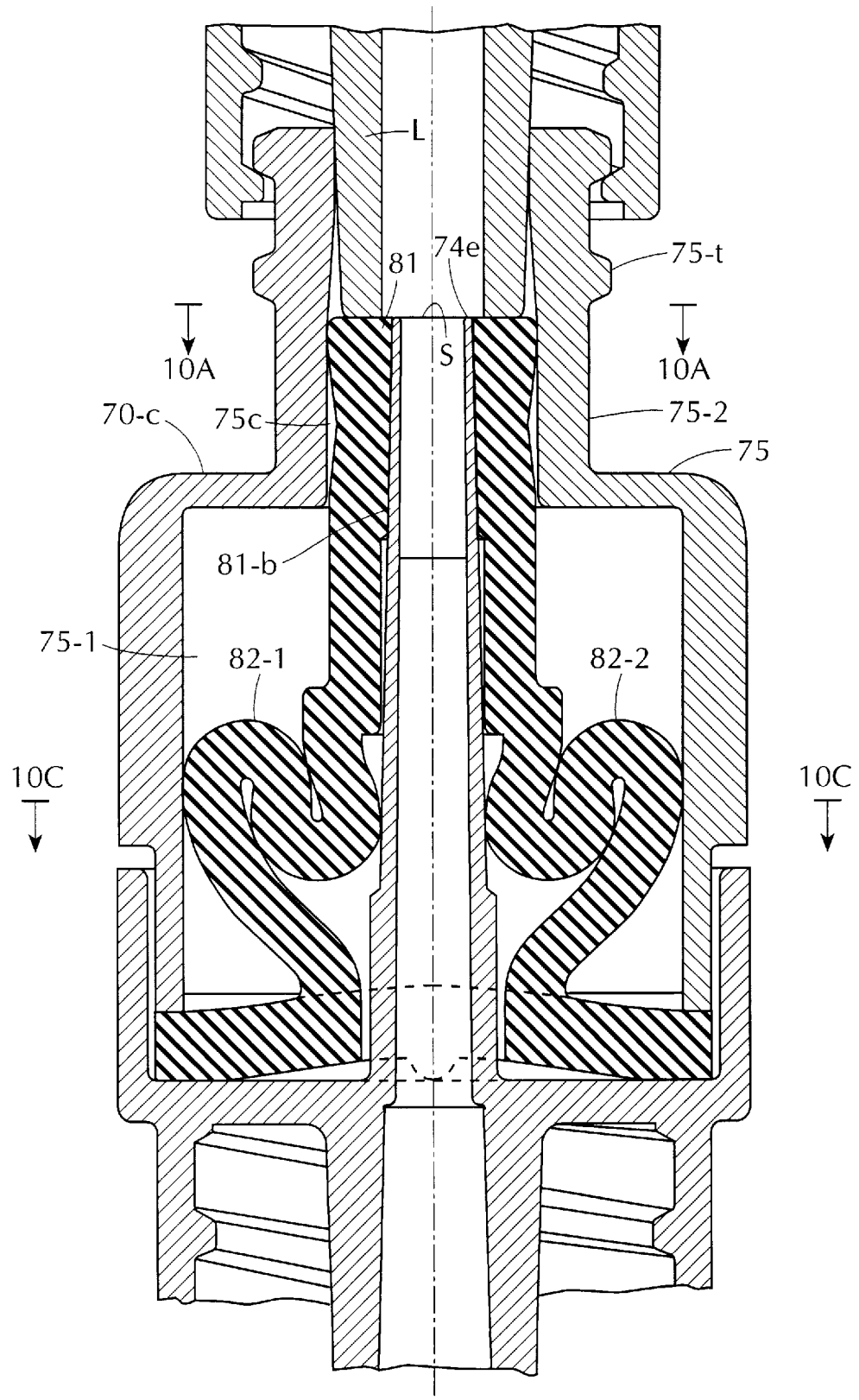
FIG. 8B is a partial, enlarged sectional view of the flow-control valve of FIG. 7C in its initial "operational flow" position with an external pressure member.

The depressible plug or movable member 80 (as shown further in FIGS. 8B through 8C) has a flexible head 81 which seals the inlet 71 and extends to a flexible body 82 for controlling flow by the outward flexing of the body 82 when the head 81 is depressed as indicated in FIG. 8B. The base 83 of the flexible body 82 sits in a rectangular well 73 of base portion 70-*b* of the valve 70. In addition, the central portion of the well 73 is bounded by an upstanding, enclosed channel forming a blunt-end cannula 74. The cannula 74, which surrounds the outlet 72, provides a closed passage from the hollow portion of the head 81 though the outlet 72.

In effect, the plug 80 forms a bell-shaped member with a hollow head 81 and a slotted body 82. The base of the body 82 terminates in a circumferential rectangular base 83. The rectangularity avoids twisting of the body 82 during compression.

In the flow control device 70, the movable plug 80, together with the head 81 and the flexible body 82, extends between the inlet 71 and the outlet 72. The flexible body 82 is expandable laterally, along a single rectangular axis, with respect to the vertical axis A of the outlet channel 72 in order to create spring pressure during opening and closing of the slit S by movement relative to the cannula 74. consequently the upper housing or cap 70-*c* has an enlarged expansion chamber 75-1. In addition, the housing 75 has a neck 75-2 with exterior Luer threads 75-*t* and an inwardly tapered bore 75-*b*1 beyond an interior cylindrical rim 75-*r*. Extending from the inwardly tapered bore 75-*b*1 is a cylindrical bore 75-*c* which, in turn, extends to a rectangular bore 75-*b*2 of the expansion chamber 75-1.

A shoulder 84 of the plug 80 engages a rectangular stop 75-*s*, and the head 81 seals the inlet 71 by being compressed against the cylindrical rim 75-*r* as described below. The head 81 is in compression sealing contact with end 74-*e* of the blunt ended, tubular cannula 74 at the bore at 81-*b*. In the open area 81-*a* below the slit S, the head 81 includes inclined wedges 81-*w* to provide a mechanical in having the tubular cannula 74 open the slit S by downward movement of a Luer tip into the rim 75-*r*.

Figure 8C:
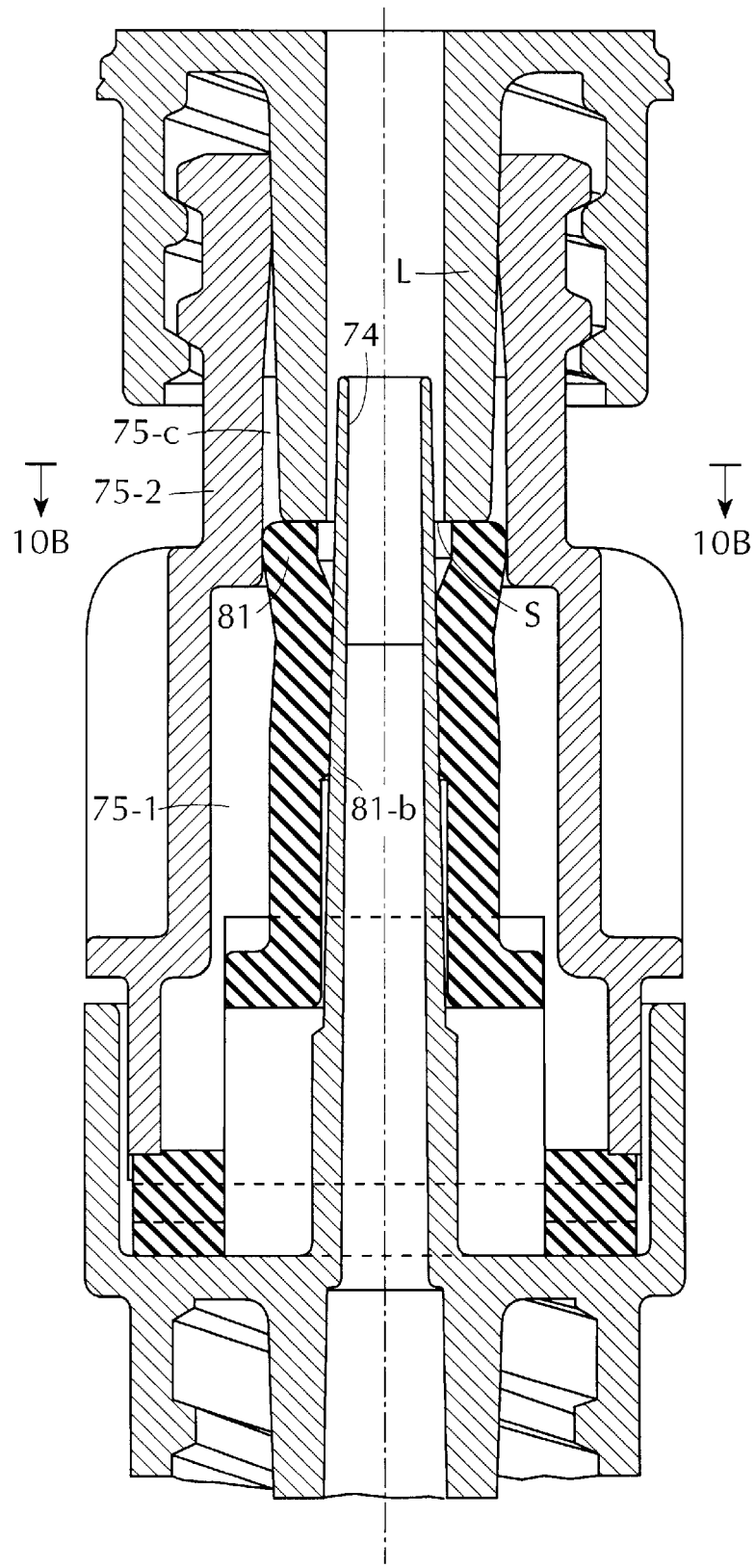
FIG. 8C is a partial, enlarged sectional view of the flow-control valve of FIG. 7C in its further "operational flow" position with an external pressure member.

The fully open position of the slit S is reached as shown in FIG. 8B when the swabbable surface of the head 81 coincides with the end 74-*e* of the blunt cannula 74. Further downward movement of the Luer tip, as shown in FIG. 8C causes the Luer tip to straddle the upper portion of the cannula 74, while maintaining a seal of the head 81 with the bore 75-*c*.

Figure 10A:
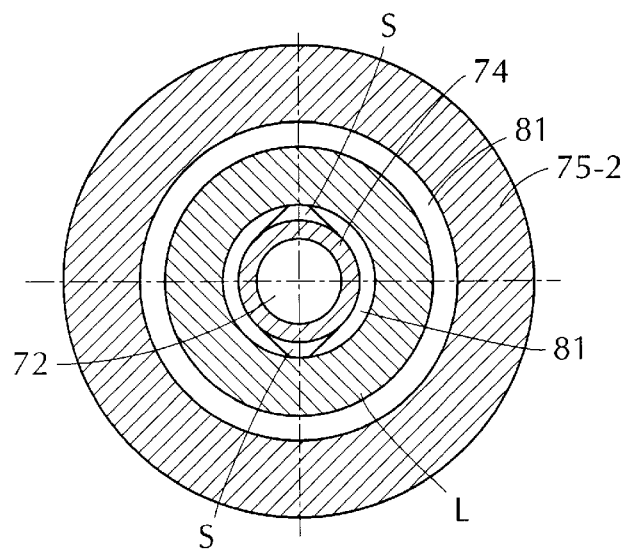
FIG. 10A is a sectional view of the flow-control valve of FIG. 8B taken along the lines 10A.
Figure 10B:
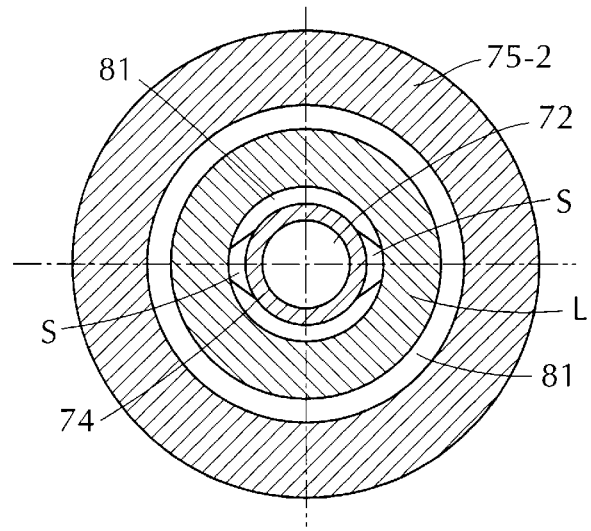
FIG. 10B is a sectional view of the flow-control valve of FIG. 8B taken along the lines 10B—10B.
Figure 10C:
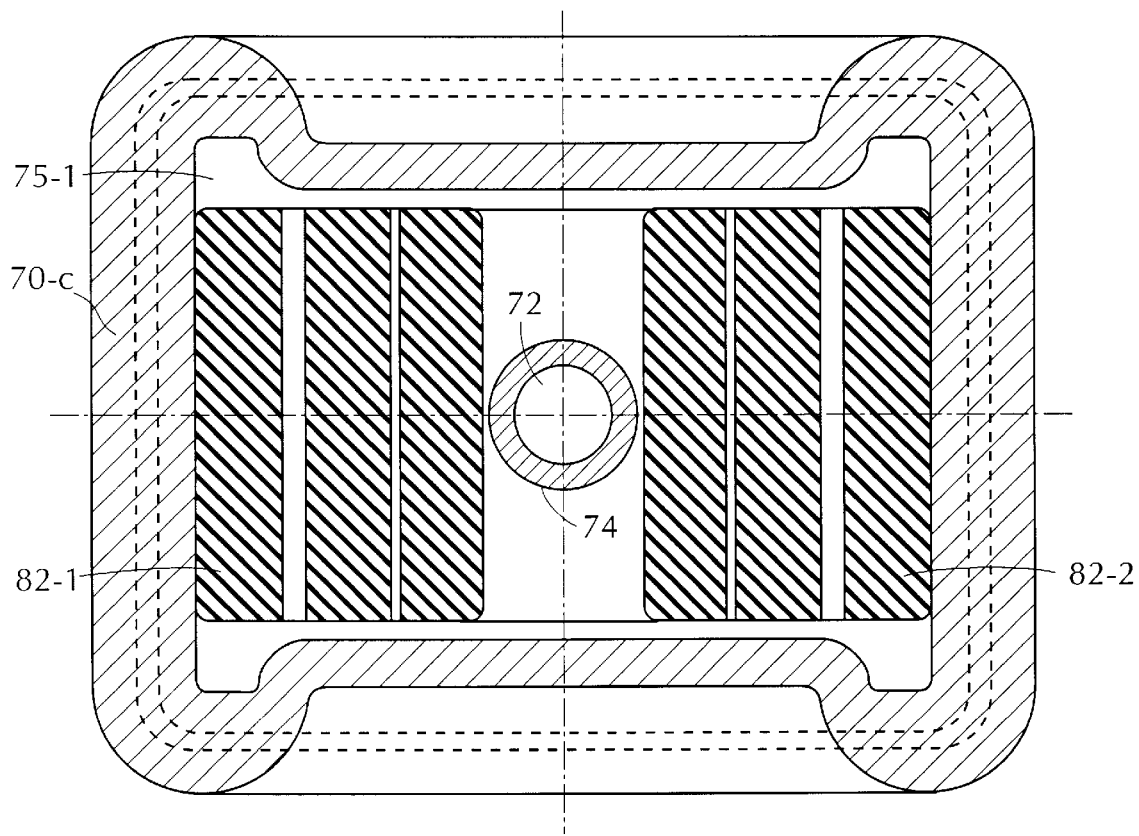
FIG. 10C is a sectional view of the flow-control valve of FIG. 8B taken along the lines 10C.

Within the expansion chamber 75-1 the two legs of the body 82 are spaced from the chamber walls as shown in FIG. 10C.

For the embodiment of FIGS. 8A–8C and 9A–9C, the head 81 of the plug 80 has an upper slit S so that when a Luer tip, such as the tip L of FIG. 8B is threaded on the neck 75-2 it seals circumferentially on top of plug 80 and there is no impediment to flow from the interior of the tip L. This embodiment is particularly useful for relative low pressure infusion of fluids, e.g. by gravity flow from a saline bag (not shown). It is to be noted that because of the slit S and the cannula 74, pressure against the outer surface of the head 81 does not cause a collapse of material which could block the tip L.

The Luer tip L thus permits activation of the control plug by a member external to the flow control device 70 since the plug 80 is seated in the inlet 71 and can be depressed from its compressed seal position to the bore 75-*r*. In effect the control is by a bell-shaped member with its upper portion sealing the inlet, and walls straddling the cannula 74. The walls are extended legs 82-1 and 82-2 which are folded under pressure as shown in FIG. 8B. The walls 82-1 and 82-2 extend from the head 81 sealing the inlet 71 to the base 73 of the lower body 70-*b* encircling the upwardly extending cannula 74.

Figure 9A:
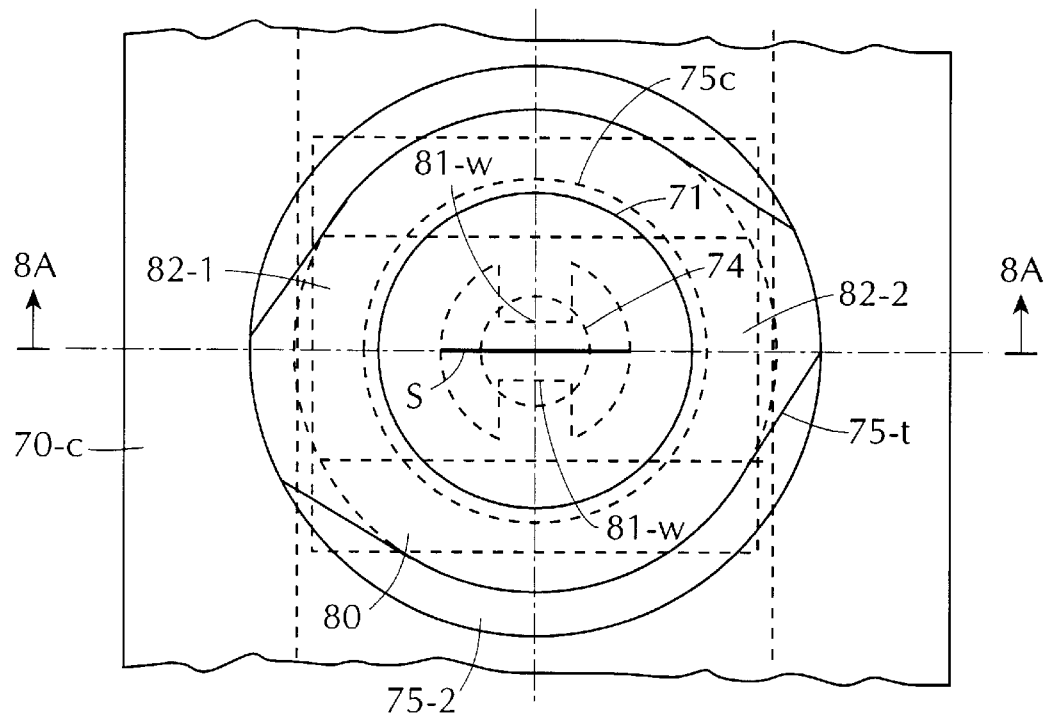
FIG. 9A is a partial and enlarged top view of the flow control valve of FIG. 7C related to FIG. 8 taken along the lines 9A.

FIG. 9A is a partial and enlarged top view of the flow control valve of FIG. 7C and is related to FIG. 8A, which is taken along the lines 9A—9A.

Figure 9B:
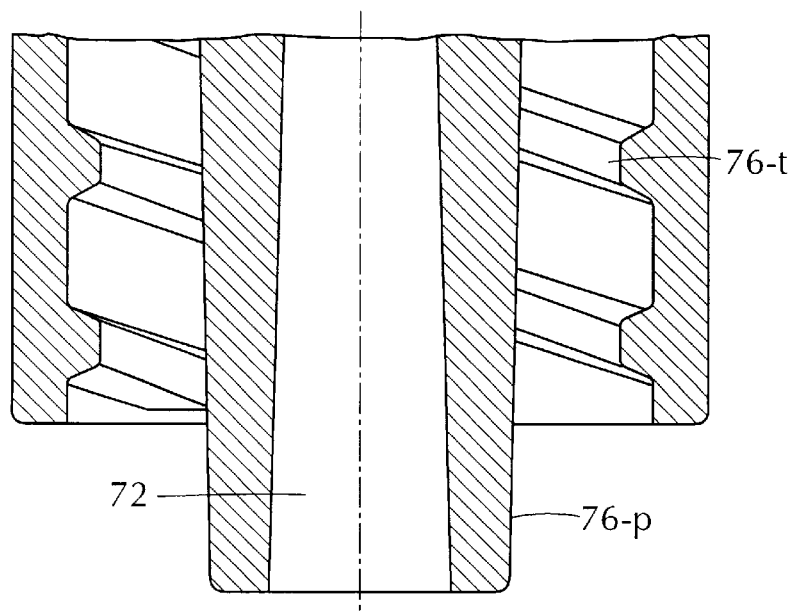
FIG. 9B is a partial view of the outlet portion of FIGS. 8A through 8C.

FIG. 9B is a partial view of the outlet portion of FIGS. 8A through 8C, showing a Luer taper 76-*p* and Luer threads 76-*t*.

Figure 9C:
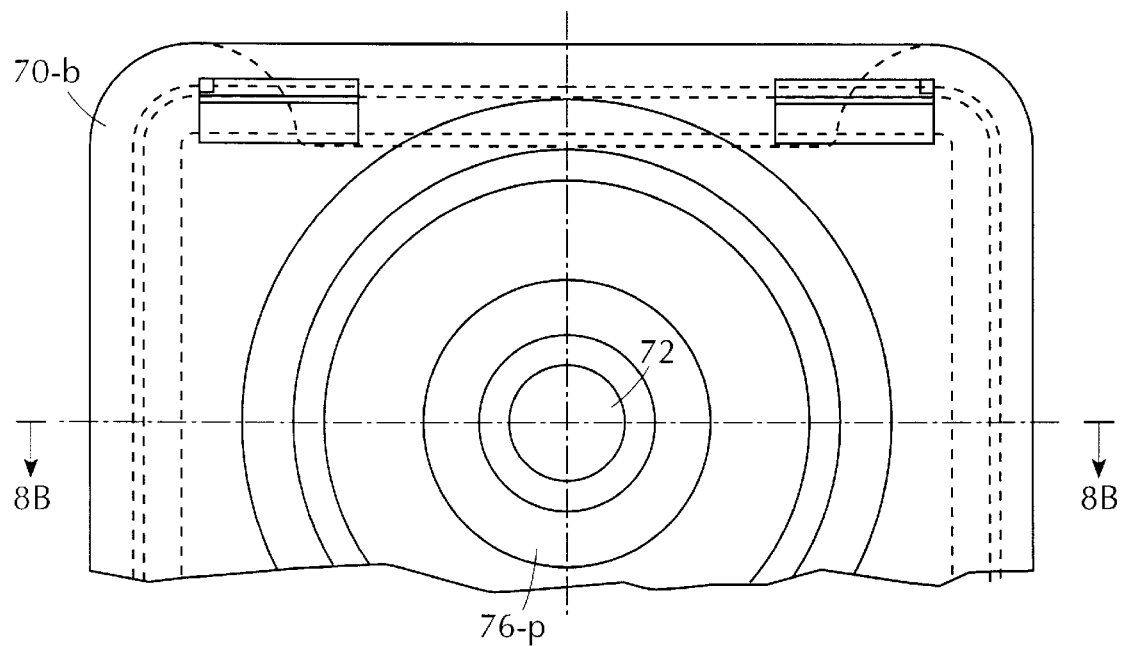
FIG. 9C is a partial bottom view of FIGS. 8A through 8C taken with respect to FIG. 9B.

FIG. 9C is a partial bottom view of FIGS. 8A through 8C and is related to FIG. 8B, which is taken along the lines FIG. 8B is taken along the lines 8B—8B of FIG. 9C. FIG. 10A is a sectional view of the flow-control valve of FIG. 8C taken along the lines 10A—10A and shows a central free-flow passage without any impedance to flow.

FIG. 10B is a sectional view of the flow-control valve of FIG. 8B taken along the lines 10B—10B and also shows a central free-flow passage without any impedance to flow.

FIG. 10C is a sectional view of the flow-control valve of FIG. 8B taken along the lines 10C—10C and shows further the folding that takes place when the legs 82-1 and 82-2 are folded.

Figure 11B:
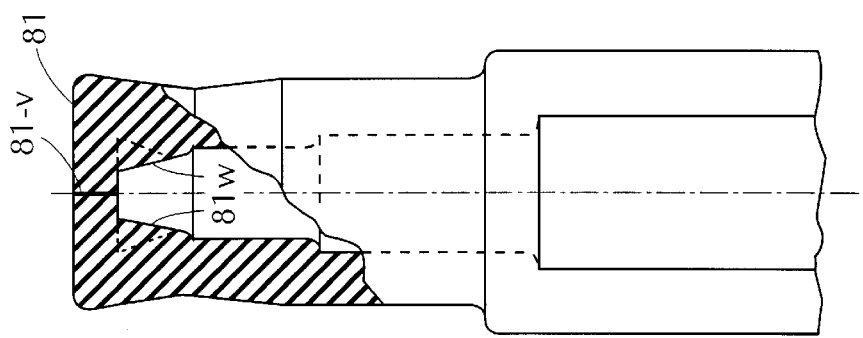
FIG. 11B is a view of the flow-control plug of FIG. 11A, rotated 90° around the vertical axis of the plug.
Figure 11C:
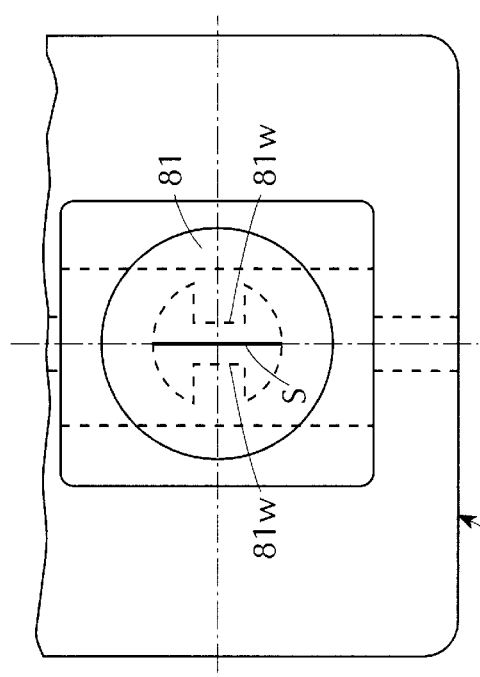
FIG. 11C is a partial top view of the plug of FIG. 11B.
Figure 11A:
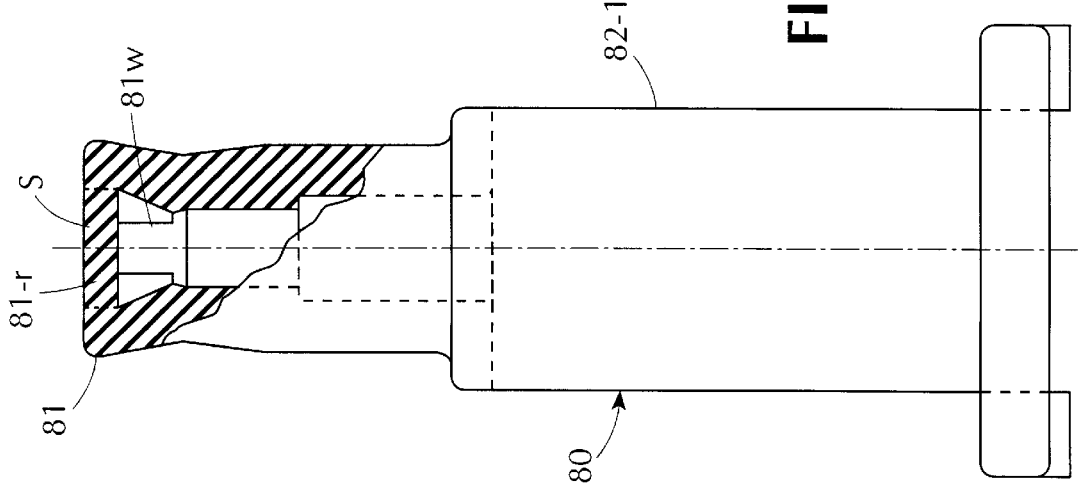
FIG. 11A is an enlarged view of the flow-control plug of FIG. 8A in its "pre-operation" condition.

FIG. 11A is an enlarged view of the flow-control plug of FIG. 8A in its "pre-operation" condition. The top portion is broken away to show details of the head 81, with the slit S extending horizontally to form a rectangular area 81-r.

FIG. 11B is a view of the flow-control plug of FIG. 11A, rotated 90° around the vertical axis of the plug of FIG. 11. Again, the top portion is broken away to show details of the head 81, with the slit S appearing as a vertical line 81-v.

FIG. 11C is a partial top view of the plug of FIG. 11B with the slit S extending beyond the length of the inclined wedges 81-w.

The component elements 70-b and 70-c are locked together by snap action. For that purpose the complementary snap-lock elements (not shown) are circumferentially spaced on the elements 70-b and 70-c, with the base of the plug wedged between them. Alternatively, the elements 70-b and 70-c can be joined, for example, by ultrasonic welding. The valves of the invention promote sterility by providing ease of accessibility. Prior art valves with recessed stoppers allow antimicrobial agents to accumulate in puddles on the tops of stoppers. Particulate matter may also collect on recessed tops.

Third Embodiments

Figure 12B:
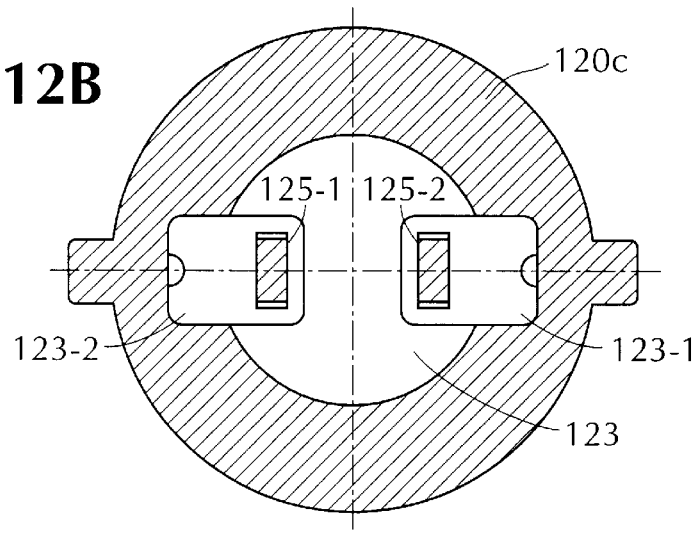
FIG. 12B is a sectional view of the flow-control valve of FIG. 12A taken along the lines 12B—12B.
Figure 12A:
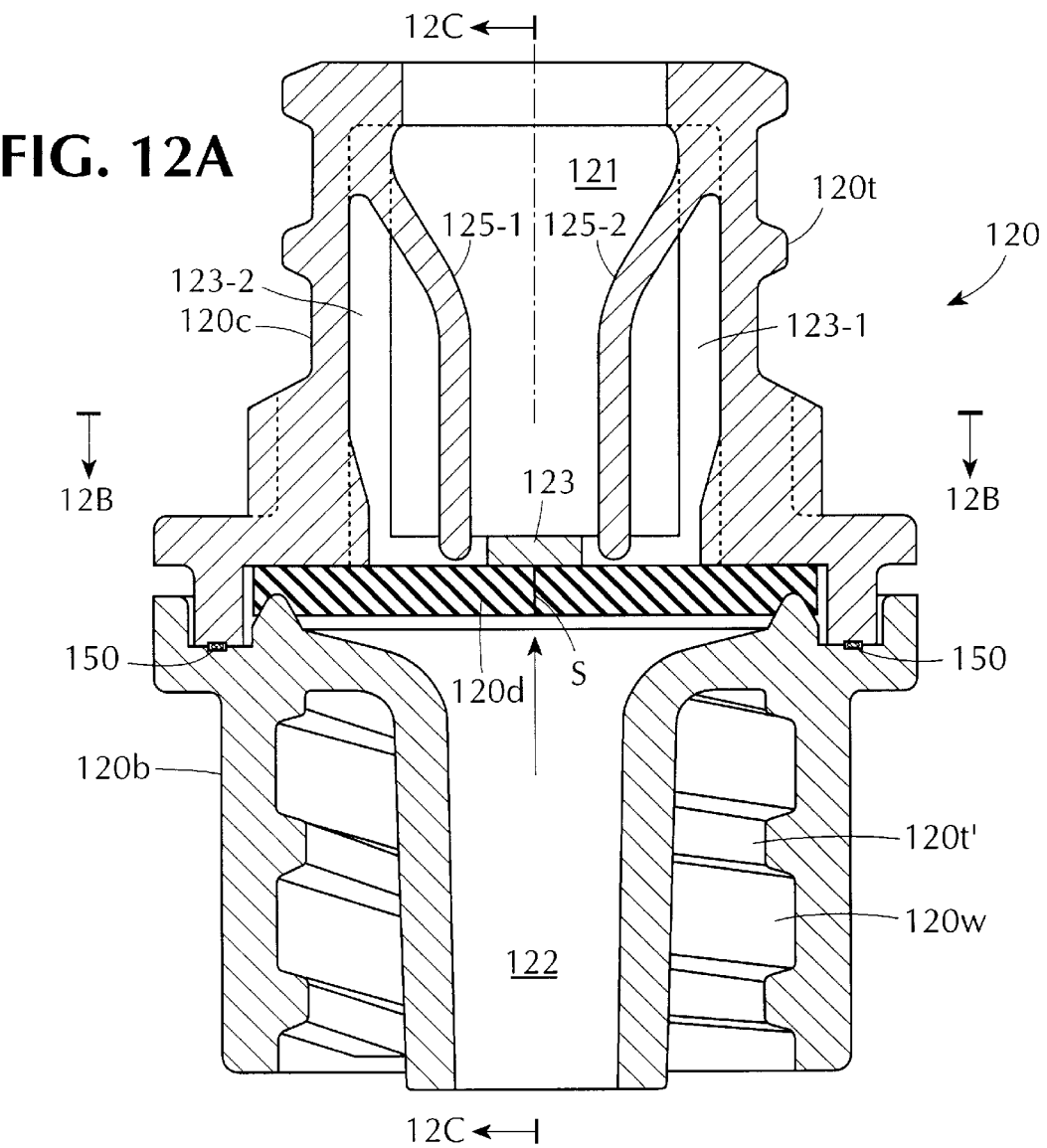
FIG. 12A is a flow-control valve in accordance with the invention for use with a Luer fitting, such as that of FIGS. 1A and 1B, with the valve in its closed valve position.

FIG. 12A is a slitted-disk check (flow-control) valve 120 in accordance with the invention for use with a Luer fitting, such as that of FIGS. 1A and 1B, with the valve 120 in its closed valve position.

As indicated in the enlarged cross-sectional view of FIG. 12A, the device 120 is formed by a base 120b and a cap 120c. The cap 120c contains an inlet flow channel 121, and the base has an outlet flow channel 122.

Both the cap 120c and the base 120b are adapted to receive flow fittings, such as a tubing (not shown), and Luer fittings, as shown.

Flow with respect to the channels 121 and 122 is selectively controlled in accordance with the operation of a control diaphragm or disk 120d that seals or "checks" the channel 121 when there is upward flow in the channel 122, and opens when there is downward flow in the channel 121.

In FIG. 12A the disk 120d is tightly secured by being clamped between the cap 120c and the base 120b, and is of circular elastomeric material. Structurally the disc 120d has opposed surfaces and a central slit S. In order to assure the "check" condition, the cap 120c has a structure 123 spaced from the disk 120d for limiting the deformation thereof in the direction of pressure through the outlet 122 to the disk 120d.

In the particular embodiment of FIGS. 12A, the slit S in the disk 120d is linear, but the slit S may also be nonlinear. In either case the limiting structure 123 desirably is integrated into the cap 120c and extends across said inlet member. Also integrated into the cap 120c are arms 125-1 and 125-2 which are shown downwardly extending from the inlet 121 into apertures of the limiting structure 123.

As shown in FIG. 12B, the limiting structure 123 is an apertured disk extending across the inlet 121, and is non-centrally apertured with a plurality of illustrative openings 123-1 and 123-2 that are symmetrically and oppositely disposed.

Figure 13:
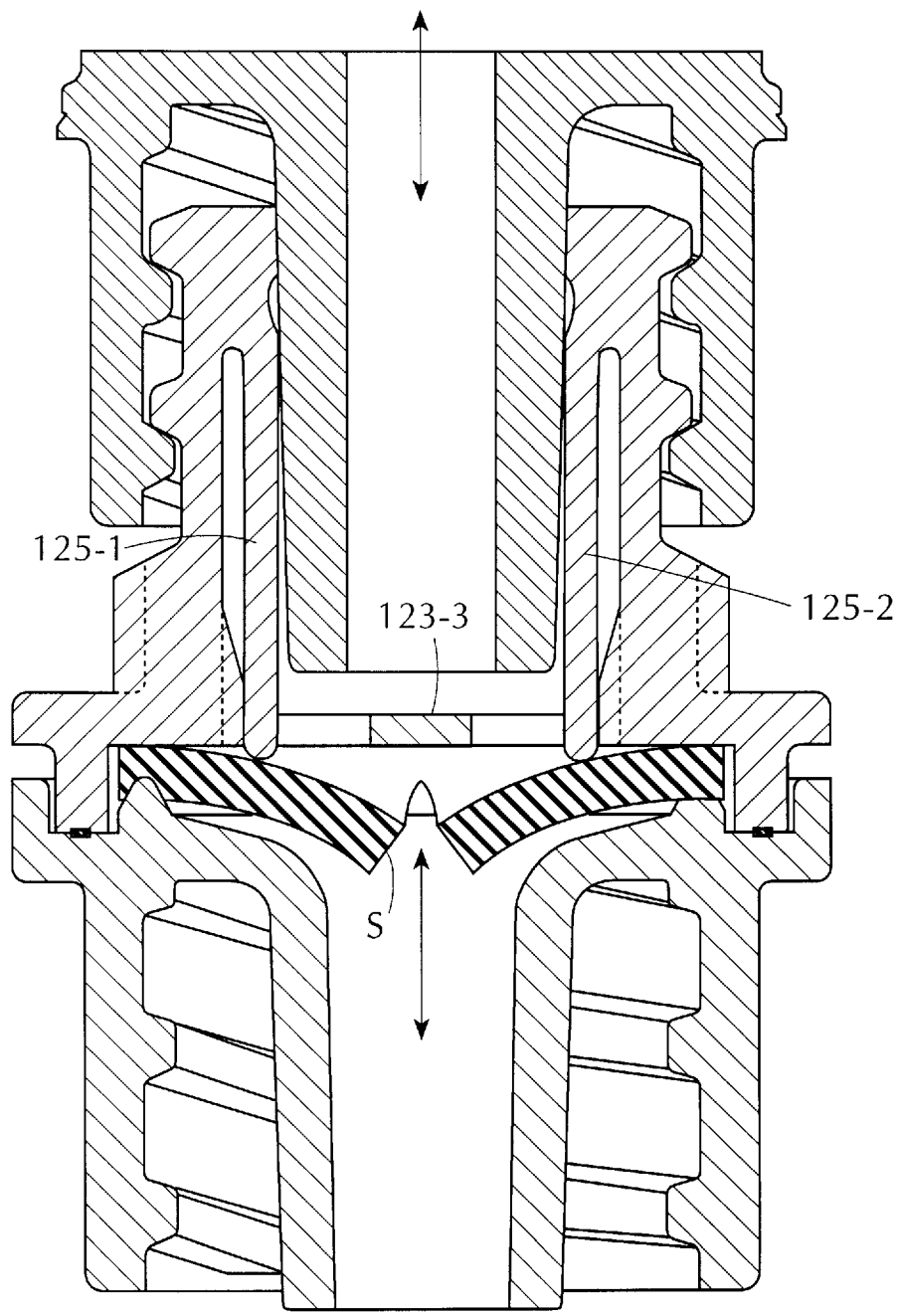
FIG. 13 is a partial, enlarged sectional view of the flow-control valve of FIG. 12A in an "operational flow" position with an external pressure member.

In effect, the limiting structure 123 has a portion 123-3 for facilitating the deformation of the disk 120d as shown in FIG. 13. The portion 123-3 spans the inlet member 120c and extends short of the position where the disk is clamped.

The component elements of the device 120 are joined, for example, by ultrasonic welding as represented by item 150 in FIG. 12A. Upon assembly the diaphragm or disc 120d is securely held in position. The inlet member 120c has a thread 120t specially designed to receive a Luer fitting. The body portion 120b has an inner wall 120w provided with threads 120t' for attachment to a suitable flow structure. The central tubular portion constitutes an outer Luer taper 120p with an inner outlet opening.

Figure 12C:
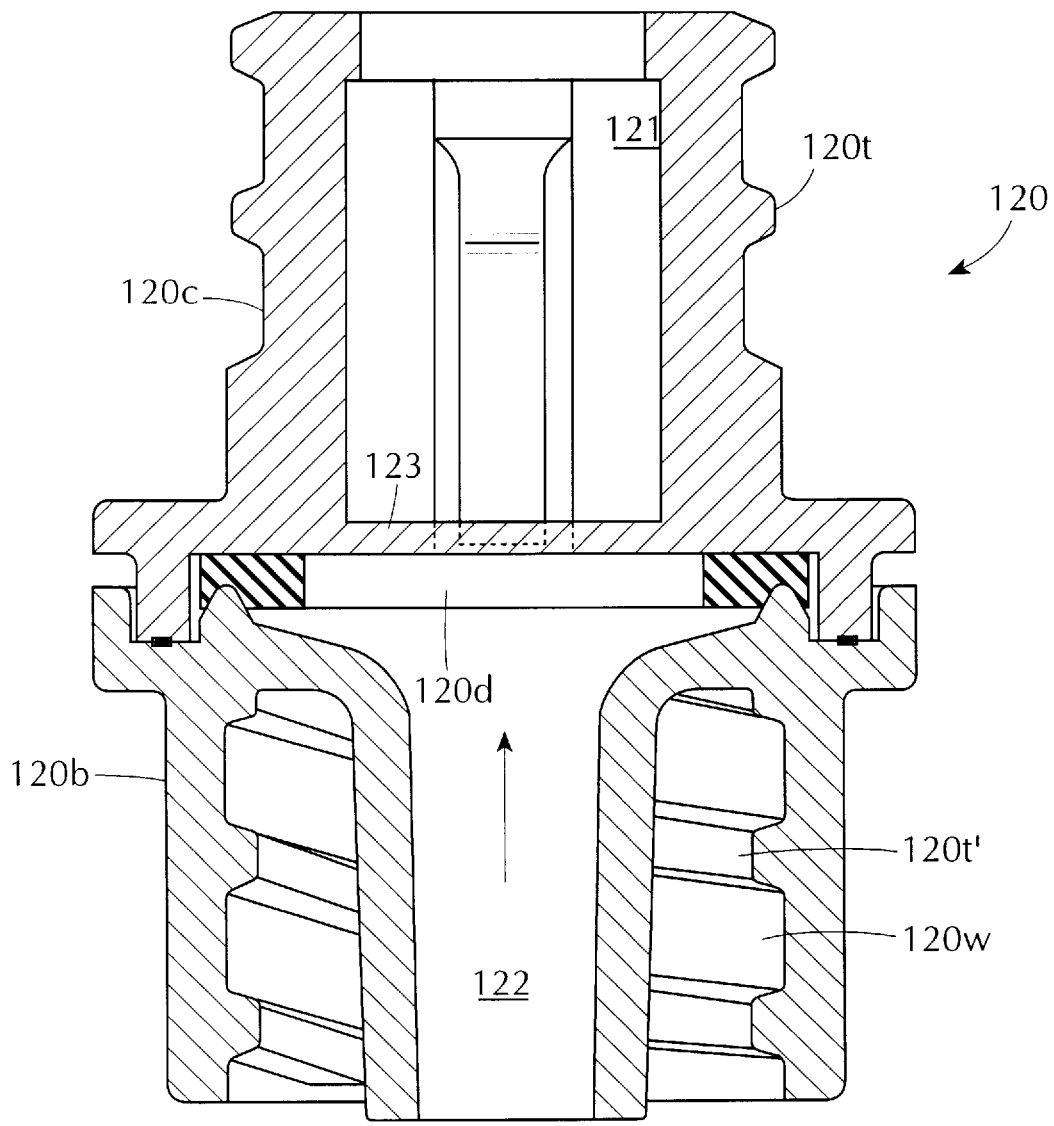
FIG. 12C is a sectional view of the flow-control valve of FIG. 12A taken along the lines 12C—12C.

FIG. 12B is a sectional view of the flow-control valve of FIG. 12A taken along the lines 12B—12B, and FIG. 12C is a sectional view of the flow-control valve of FIG. 12A taken along the lines 12C—12C.

In FIG. 13, which is a partial, enlarged sectional view of the flow-control valve of FIG. 12A in an "operational flow" position, an external Luer pressure member has spread the arms 125-1 and 125-2, causing their tip portions to open the disk 120d independently of downward flow.

Figure 14A:
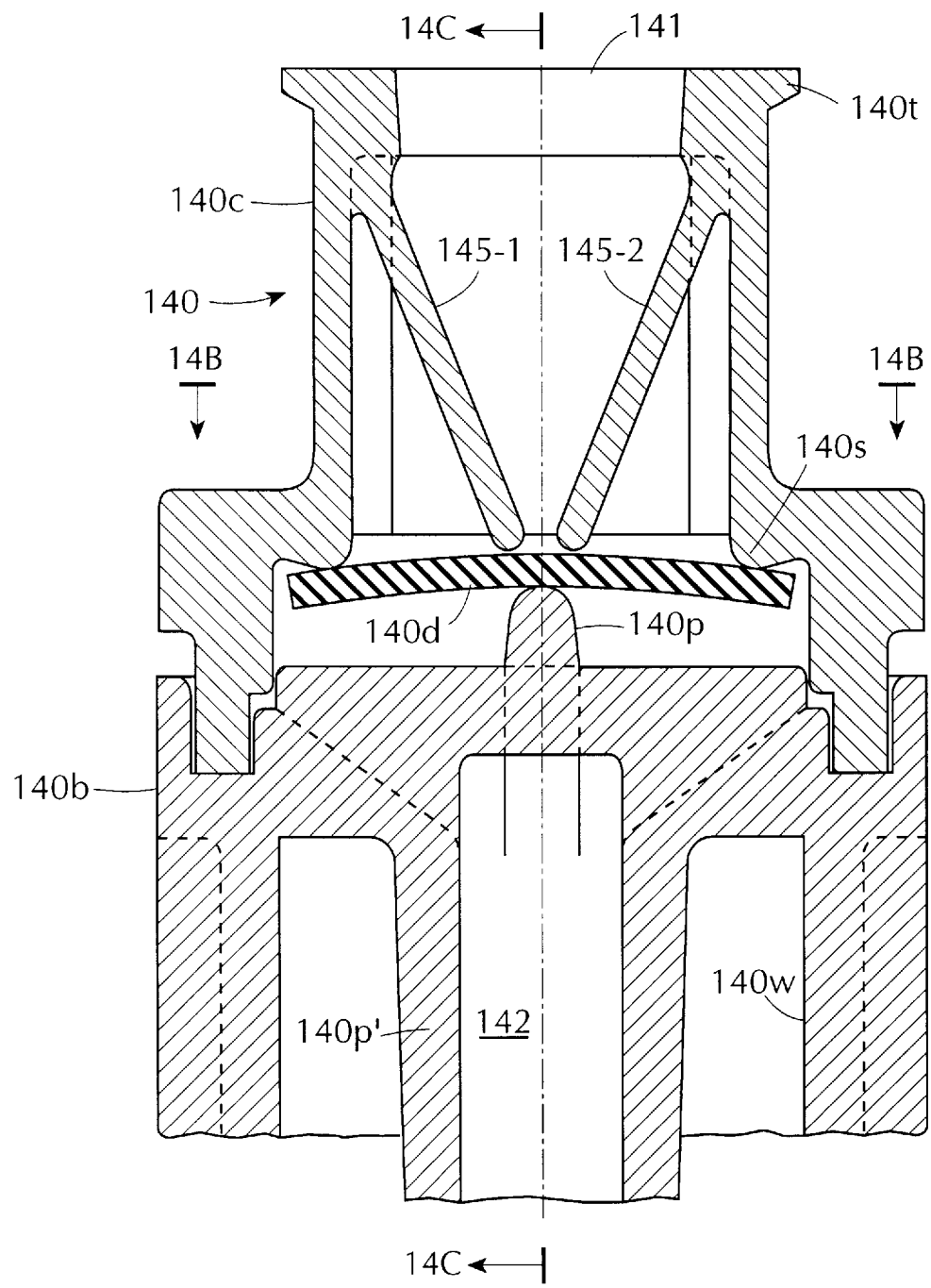
FIG. 14A is another flow-control valve in accordance with the invention for use with a Luer fitting, such as that of FIGS. 1A and 1B, with the valve in its closed valve position.

FIG. 14A is another flow-control valve 140 in accordance with the invention for use with a Luer fitting, such as that of FIGS. 1A and 1B, with the valve 140 in its closed valve position. As indicated in the enlarged cross-sectional view of FIG. 12A, the device 140 is formed by a base 140b and a cap 140c. The cap 140c contains an inlet flow channel 141, and the base has an outlet flow channel 142.

Both the cap 140c and the base 140b are adapted to receive flow fittings, such as a tubing (not shown), and Luer fittings, as shown.

Flow with respect to the channels 141 and 142 is selectively controlled in accordance with the operation of a control diaphragm or disk 140d that seals or "checks" the channel 141 when there is upward flow in the channel 142, and opens when there is downward flow in the channel 141. In FIG. 14A the disk 140d is "biased", i.e. positioned, against an annular seat 140s of the cap 140c by a central prong 140p extending from the base 140b, and is of circular elastomeric material.

Also integrated into the cap 140c are arms 145-1 and 145-2 which are shown downwardly extending from the inlet 141 to a position above the disk 140d and straddling the prong 140p.

The component elements of the device 140 are joined, for example, by ultrasonic welding. Upon assembly the diaphragm or disc 140d is securely held in position.

The inlet member 140c has a thread 140t specially designed to receive a Luer fitting. The body portion 140b has an inner wall 140w for attachment to a suitable flow structure. The central tubular portion constitutes an outer Luer taper 140p with an inner outlet opening.

Figure 14B:
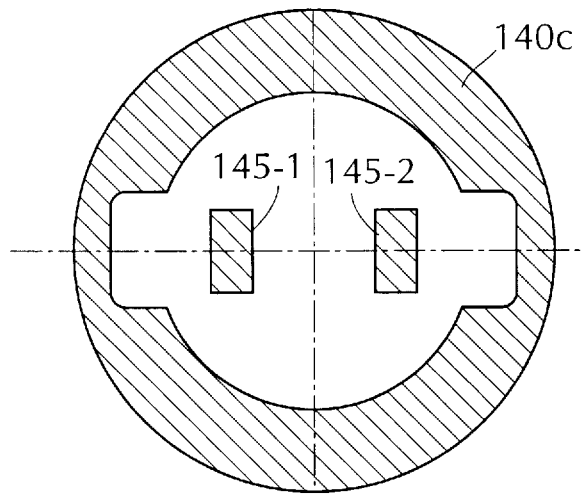
FIG. 14B is a sectional view of the flow-control valve of FIG. 14A taken along the lines 14A—14A.
Figure 14C:
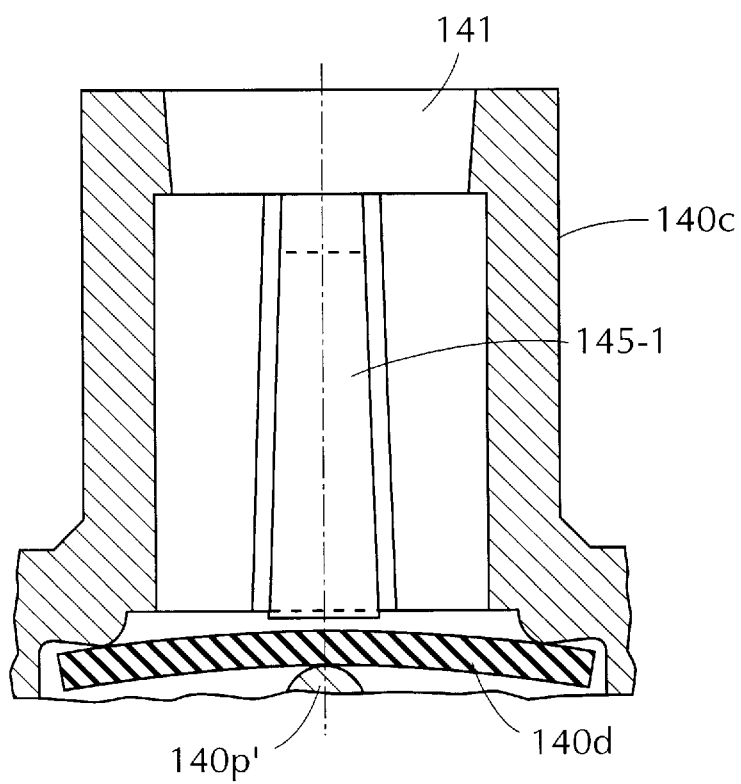
FIG. 14C is a sectional view of the flow-control valve of FIG. 14A taken along the lines 14C—14C.

FIG. 14B is a sectional view of the flow-control valve of FIG. 14A taken along the lines 14B—14B, and FIG. 14C is a sectional view of the flow-control valve of FIG. 14A taken along the lines 14C—14C.

Figure 15:
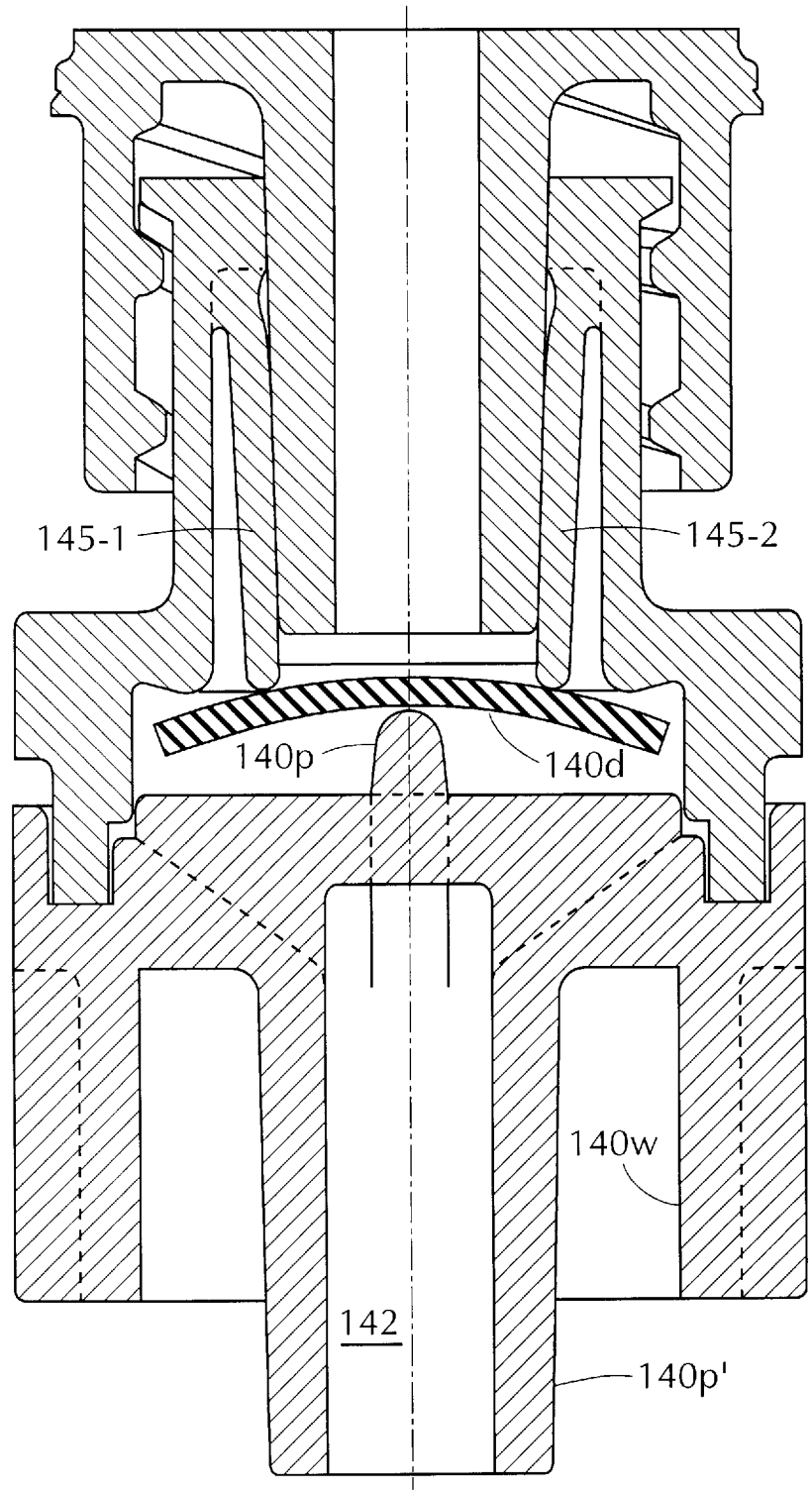
FIG. 15 is a partial, enlarged sectional view of the flow-control valve of FIG. 14A in an "operational flow" position with an external pressure member.

In FIG. 15, which is a partial, enlarged sectional view of the flow-control valve of FIG. 14A in an "operational flow" position, an external Luer pressure member has spread the arms 145-1 and 145-2, causing their tip portions to unseat the disk 140d from the seat 140s independently of downward flow.

It will be understood that the foregoing embodiments are illustrative only and that modifications and adaptations of the invention may be made without departing from its spirit and scope as defined in the appended claims.

What is claimed:

1. A flow control device comprising:
   a valve body having an inlet and an outlet, the inlet having a circumferential end wall, the valve body further comprising a substantially rectangular well and an upstanding tubular cannula extending from a central portion of the well, towards the inlet, the tubular cannula having a first portion proximate the inlet and a bore with a first open end in the first portion and a second open end at the outlet for providing a passage for fluid to flow from the inlet to the outlet; and
   a movable plug comprising a flexible head with a closed slit, the flexible head having a first position sealing the inlet, the flexible head being flush with the circumferential end wall of the inlet when in the first position, thereby facilitating antiseptic swabbing of the plug,
   the movable plug further comprising a flexible body coupled to the flexible head, the flexible body comprising elongated legs sitting in the well of the valve body, such that when the flexible head is moved to a second position over the first portion of the tubular cannula, the slit is opened, enabling the flow of fluid through the passage of the tubular cannula and the elongated legs are flexed, providing a return force for returning the flexible head to its first position.

2. The flow control device of claim 1, wherein the valve body has an exterior surface with a rectangular exterior cross-section.

3. The flow control device of claim 2, wherein the flexible head has an internal open area below the slit, the open area including inclined wedges to provide a mechanical advantage for opening the slit when the flexible head is moved from the first position to the second position over the first portion of the tubular cannula.

4. The flow control device of claim 3, wherein the flexible head has a bore portion below the inclined wedges, the bore portion having an inner surface in sealing contact with the first portion of the tubular cannula when the flexible head is in the first position.

5. The flow control device of claim 4, wherein the inner surface is in sealing contact with an outside wall of the tubular cannula as the flexible head is moved from the first position to the second position.

6. The flow control device of claim 3, further including means for permitting the depression of the flexible head by a member external thereto, over the tubular cannula.

7. The flow control device of claim 6, wherein the external member has a tip with a Luer taper.

8. The flow control device of claim 6, wherein the inlet extends to a tapered bore which is spaced from the movable plug, the tapered bore providing space for the flexible head to expand into, as the flexible head is moved from the first position to the second position.

9. The flow control device of claim 8, wherein the tapered bore leads to a bore portion with an essentially constant diameter adjacent the first portion of the tubular cannula.

10. The flow control device of claim 6, wherein the flexible head has a top portion including an exterior circumferential side wall tapered outwardly toward the circumferential end wall of the inlet when the flexible head is in the first position, whereby the taper of the flexible head promotes the sealing of the inlet.

11. The flow control device of claim 1, wherein the legs flex outwardly when the movable plug is depressed.

12. A flow control device comprising:
    a valve body having an inlet, an outlet, a well with a central portion and a tubular cannula extending from the central portion toward the inlet, the tubular cannula having a first portion proximate the inlet, a bore with a first open end in the first portion and a second open end at the outlet, the bore providing a passage for fluid to flow from the inlet to the outlet;
    a plug comprising a flexible body, a base sitting in the well of the valve body and a flexible head coupled to the flexible body, the flexible head sealing the inlet and having a closed slit with a longitudinal axis;
    the first portion of the tubular cannula and the flexible head being engageable with each other to open the slit, and the flexible head having an open area below the slit including two opposed inclined wedges each having flat surfaces converging towards the longitudinal axis of the slit for providing a mechanical advantage as the first portion of the tubular cannula opens the slit by engaging the inclined wedges.

13. A flow control device comprising:
    a valve body having an inlet, an outlet, a well with a central portion, a tubular cannula extending from the central portion toward the inlet, the tubular cannula having a first portion proximate the inlet and a bore having a first open end in the first portion and a second open end at the outlet for providing a passage for fluid to flow from the inlet to the outlet;
    a movable plug comprising a flexible body having a base sitting in the well of the valve body, a flexible head coupled to the flexible body and having a closed slit, the flexible head having a position sealing the inlet, the flexible head being depressible over the first portion of the tubular cannula from the position sealing the inlet, to open the slit; and
    the valve body further comprising a tapered bore extending from the inlet, the tapered bore being spaced from the movable plug such that when the flexible head of the movable plug is depressed over the first portion of the tubular cannula, the flexible head expands into the tapered bore.

14. The flow control device of claim 13, wherein the inlet has a first portion at its external end with a first diameter and the valve body has a tapered portion and an interior portion with a second diameter greater than the first diameter, wherein the first portion is connected to the interior portion through the tapered portion.

15. The flow control device of claim 14, wherein the flexible head has an internal open area below the slit, including inclined wedges for providing a mechanical advantage as the first portion of the tubular cannula opens the slit by engaging the inclined wedges.

16. The flow control device of claim 15, wherein the valve body has a rectangular cross-section.

17. A flow control device comprising:
    a valve body having an inlet and an outlet, the inlet having a circumferential end wall, the valve body further comprising a well and an upstanding tubular cannula extending from a central portion of the well, towards the inlet, the tubular cannula having a first portion proximate the inlet and a bore with a first open end in the first portion and a second open end at the outlet for providing a passage for fluid to flow from the inlet to the outlet; and
    a movable plug comprising a flexible head with a closed slit, the flexible head having a first position sealing the inlet, the flexible head being flush with the circumferential end wall of the inlet while in the first position, thereby facilitating antiseptic swabbing of the plug, the movable plug further comprising a flexible body coupled to the flexible head, the flexible body comprising elongated legs sitting in the well of the valve body, such that when the flexible head is moved to a second position over the first portion of the tubular cannula, the slit is opened, enabling the flow of fluid through the passage of the tubular cannula and the elongated legs are flexed, providing a return force for returning the flexible head to its first position.

18. The flow control device of claim 17, wherein the flexible body comprises two opposed, elongated legs, each having a first portion proximate the flexible head and a second portion sitting in the well, wherein the distance between the first portions of each leg is less than the distance between the second portions of each leg.

19. The flow control device of claim 18, wherein the well is substantially rectangular and the second portion of the legs are connected to a substantially rectangular base sitting in the well.

20. The flow control device of claim 18, wherein when the legs are sufficiently flexed by movement of the flexible head from the first position to the second position, the legs fold over themselves.

21. The flow control device of claim 20, wherein the well is substantially rectangular and the second portion of the legs are connected to a substantially rectangular base sitting in the well.

22. A flow control device comprising:

a valve body having an inlet and an outlet, the inlet having a circumferential end wall, the valve body having an exterior surface with at least one flat side for being positioned on the surface of a patient, the valve body further comprising an internal well and an upstanding tubular cannula extending from a central portion of the well, towards the inlet, the tubular cannula having a first portion proximate the inlet and a bore with a first open end in the first portion and a second open end at the outlet for providing a passage for fluid to flow from the inlet to the outlet; and a movable plug comprising a flexible head with a closed slit, the flexible head having a first position sealing the inlet, the flexible head being flush with the circumferential end wall of the inlet while in the first position, thereby facilitating antiseptic swabbing of the plug, the movable plug further comprising a flexible body coupled to the flexible head, such that when the flexible head is moved to a second position over the first portion of the tubular cannula, the slit is opened, enabling the flow of fluid through the passage of the tubular cannula and the flexible body is flexed, providing a return force for returning the flexible head to its first position.

* * * * *

UNITED STATES PATENT AND TRADEMARK OFFICE
CERTIFICATE OF CORRECTION

PATENT NO. : 5,806,831

DATED : September 15, 1998

INVENTOR(S) : Joseph R. Paradis

It is certified that error appears in the above-indentified patent and that said Letters Patent is hereby corrected as shown below:

Column 2, line 41, after "Pat." Insert --No.--;

Column 5, line 22, remove "for";

Column 5, line 24, remove "for";

Column 5, line 56, change "9A" to --9A-9A--;

Column 5, line 63, change "10A" to --10A-10A--;

Column 5, line 67, change "10C" to --10C-10C--;

Column 10, line 14, remove "until", second occurrence;

Column 10, line 18, after mechanical, insert --advantage as the--;

Column 10, line 34, after "the top of" insert --the--;

Column 10, line 60, remove "and is related to Fig.8B, which is taken along the lines"

Claim 8, after "claim", change "6" to --5--.

Signed and Sealed this

Sixteenth Day of November, 1999

Attest:

Q. TODD DICKINSON

*Attesting Officer*     *Acting Commissioner of Patents and Trademarks*